US007008957B2

(12) United States Patent
Wagner et al.

(10) Patent No.: US 7,008,957 B2
(45) Date of Patent: Mar. 7, 2006

(54) BICYCLIC CYANOHETEROCYCLES, PROCESS FOR THEIR PREPARATION AND THEIR USE AS MEDICAMENTS

(75) Inventors: Holger Wagner, Biberach an der Rib (DE); Karl Schoenafinger, Alzenau (DE); Gerhard Jaehne, Frankfurt (DE); Holger Gaul, Runkel (DE); Christian Buning, Bonn (DE); Georg Tschank, Essenheim (DE); Ulrich Werner, Miehlen (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 11 days.

(21) Appl. No.: 10/898,751

(22) Filed: Jul. 26, 2004

(65) Prior Publication Data
US 2005/0059716 A1 Mar. 17, 2005

Related U.S. Application Data

(60) Provisional application No. 60/527,697, filed on Dec. 8, 2003.

(30) Foreign Application Priority Data

Jul. 25, 2003 (DE) ................ 103 33 935

(51) Int. Cl.
A61K 31/428 (2006.01)
A61K 31/454 (2006.01)
A61K 31/5377 (2006.01)
C07D 417/02 (2006.01)
C07D 277/60 (2006.01)

(52) U.S. Cl. ............ 514/368; 548/152; 548/179; 546/198; 546/270.1; 544/133; 544/368; 540/480; 540/603; 514/321; 514/338; 514/233.2; 514/254.02; 514/217.1

(58) Field of Classification Search ........... 514/368; 548/152; 546/198
See application file for complete search history.

(56) References Cited

U.S. PATENT DOCUMENTS

| 6,221,633 | B1 | 4/2001 | Ertl et al. | |
|---|---|---|---|---|
| 6,221,897 | B1 | 4/2001 | Frick et al. | |
| 6,245,744 | B1 | 6/2001 | Frick et al. | |
| 6,329,403 | B1 * | 12/2001 | Odaka et al. | 514/342 |
| 6,342,512 | B1 | 1/2002 | Kirsch | |
| 6,380,357 | B1 | 4/2002 | Hermeling et al. | |
| 6,624,185 | B1 | 9/2003 | Glombik | |
| 6,884,812 | B1 | 4/2005 | Glombik | |

FOREIGN PATENT DOCUMENTS

| DE | 10142734 | 3/2003 |
|---|---|---|
| WO | WO 91/11457 | 8/1991 |
| WO | WO 97/26265 | 7/1997 |
| WO | WO 97/41097 | 11/1997 |
| WO | WO 99/03861 | 1/1999 |
| WO | WO 99/15525 | 4/1999 |
| WO | WO 99/31507 | 6/1999 |
| WO | WO 00/34332 | 6/2000 |
| WO | WO 03/34331 | 6/2000 |
| WO | WO 00/40569 | 7/2000 |
| WO | WO 00/63208 | 10/2000 |
| WO | WO 00/64876 | 11/2000 |
| WO | WO 00/64888 | 11/2000 |

(Continued)

OTHER PUBLICATIONS

Baures, et al., "Design, Synthesis, and Dopamine Receptor-Modulating Activity of Diketopiperazine Peptidomimetics of L-Prolyl-L-leucylglycinamine," J. Med. Chem., vol. 40, pp. 3594-3600 (1997).*
Aicher, et. al., Substitued Tetrahydroprrolo[2,1-b]Oxazol-5 (6H)-Ones and Tetrahydropyrrolo[2,1-b]Thiazol-5(6H)-Ones as Hypoglycemic Agents 1, J. Med. Chem. (1998) vol. 41, pp. 4556-4566.
Asakawa, A., et al., Cocaine-Amphetamine-Regulated Transcript Influences Energy Metabolism, Anxiety and Gastric Emptying in Mice, Hormone and Metabolic Research, 2001, vol. 33(9), pp 554-558.
Lee Daniel W et al., Leptin agonists as a potential approach to the treatment of obestiy, Drugs of the Future, 2001, vol. 26(9), pp 873-881.
Okada Hiroshi et al., Synthesis and Antitumor Activities of Prodrugs of Benzoylphenytureas, Chem. Pharm. Bull., 1994, vol. 42(1), pp 57-61.
Salvador Javier et al., Perspectives in the therapeutic use of leptin, Expert Opinion on Pharmacotherapy 2001, 2(10), 1615-1622.
Tyle, Praveen, Iontophoretic Devices for Drug Delivery, Pharmaceutical Research, vol. 3, No. 6, 1986 pp. 318-326.
Zunft, H. et al., Carob Pulp Preparation for Treatment of Hypercholesterolemia, Advances in Therapy, 2001, vol. 18(5), pp 230-236.

Primary Examiner—Joseph K. McKane
Assistant Examiner—Andrew B. Freistein
(74) Attorney, Agent, or Firm—Barbara E. Kurys

(57) ABSTRACT

The invention relates to compounds of the formula I

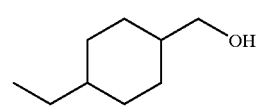

in which the radicals have the stated meanings, their stereoisomeric forms and their physiologically tolerated salts and process for their preparation.

The compounds are suitable for the treatment of metabohlic disorders such as type 2 diabetes.

10 Claims, No Drawings

FOREIGN PATENT DOCUMENTS

| | | |
|---|---|---|
| WO | WO 00/66585 | 11/2000 |
| WO | WO 00/71549 | 11/2000 |
| WO | WO 00/78312 | 12/2000 |
| WO | WO 01/04156 | 1/2001 |
| WO | WO 01/09111 | 2/2001 |
| WO | WO 01/83451 | 11/2001 |
| WO | WO 01/85695 | 11/2001 |
| WO | WO 01/91752 | 12/2001 |

* cited by examiner

BICYCLIC CYANOHETEROCYCLES, PROCESS FOR THEIR PREPARATION AND THEIR USE AS MEDICAMENTS

The invention relates to substituted cyanothiazolides and to their physiologically tolerated salts.

Compounds of similar structure and their use in a screening have already been described in the prior art (WO 99/31507).

The invention was based on the object of providing compounds which display a therapeutically utilizable blood glucose-lowering effect and are suitable in particular for the treatment of diabetes.

The invention therefore relates to compounds of the formula I,

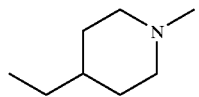

wherein

R1 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl or heterocyclyl,
  wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, OH, $-CF_3$, $(C_1-C_6)$-alkyl, $(C_2-C_6)$-alkenyl, $(C_2-C_6)$-alkynyl, OR3, NR3R4, COR3, $CO2R3$, CONR3R4, $(C_1-C_6)$-alkylene-OR3, $(C_1-C_6)$-alkylene-NR3R4, $(C_1-C_6)$-alkylene-SR3, alkylene-SOR3, alkylene-$SO_2$R3, $(C_1-C_6)$-alkylene-COR3, $(C_1-C_6)$-alkylene-COOR3, $(C_1-C_6)$-alkylene-CONR3R4, $(C_1-C_6)$-alkylene-O—P(O)(OR3)$_2$, SR3, SOR3, $SO_2$NR3R4, $SO_2$R3, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl,
    wherein said $(C_6-C_{10})$-aryl is optionally substituted one or more times by F, Cl, Br, I, CN, $NO_2$, OH, $-CF_3$, $(C_1-C_6)$-alkyl, $(C_2-C_6)$-alkenyl, $(C_2-C_6)$-alkynyl, OR3, NR3R4, COR3, $CO_2R3$ or CONR3R4,
    and wherein said heterocyclyl is optionally substituted one or more times by F, Cl, Br, I, CN, $NO_2$, OH, $-CF_3$, $(C_1-C_6)$-alkyl, OR3, NR3R4, COR3, $CO_2R3$ or CONR3R4;

R2 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, COOR3, CONR3R4 or CN,
  wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, $-CF_3$, $(C_2-C_6)$-alkenyl, $(C_2-C_6)$-alkynyl, OR3, OP(O)(OR3)$_2$, NR3R4, NR3CONR3R4, COR3, OCOR3, OCOOR3, COOR3, CONR3R4, OCONR3R4, $(C_1-C_6)$-alkylene-OR3, $(C_1-C_6)$-alkylene-NR3R4, $(C_1-C_6)$-alkylene-NR3SO$_2$R4, $(C_1-C_6)$-alkylene-SR3, alkylene-S(O)R3, alkylene-S(O)$_2$R3, alkylene-S(O)$_2$NR3R4, $(C_1-C_6)$-alkylene-COR3, $(C_1-C_6)$-alkylene-COOR3, $(C_1-C_6)$-alkylene-CONR3R4, SR3, SOR3, $SO_2$R3, $SO_2$NR3R4, NR3SO$_2$R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;

R3, R4 are each, independently of one another, H, $(C_1-C_6)$-alkyl, $-CF_3$, $(C_3-C_{10})$-cycloalkyl, $(C_6-C_{10})$-aryl, heterocyclyl, $(C_1-C_6)$-alkylene-CONR5R6, CONR5R6, $(C_1-C_6)$-alkylene-COOR5, COOR5, COR5, $(C_1-C_6)$-alkylene-COR5, $(C_1-C_6)$-alkylene-OR5, $(C_1-C_6)$-alkylene-NR5R6, $(C_1-C_6)$-alkylene-SR 5, $(C_1-C_6)$-alkylene-S(O)R5, $(C_1-C_6)$-alkylenee-S(O)$_2$R5, S(O)R5, S(O)$_2$R5, $(C_1-C_4)$-alkylene-$(C_6-C_{10})$-aryl or $(C_1-C_4)$-alkylene-heterocyclyl;

R5, R6 are each, independently of one another, H, $(C_1-C_6)$-alkyl, $(C_1-C_6)$-alkylene-$(C_6-C_{10})$-aryl, $-(C_6-C_{10})$-aryl, heterocyclyl or $(C_1-C_6)$-alkylene-heterocyclyl;

X is S, SO or $SO_2$;

and pharmaceutically acceptable salts thereof.

Preference is given to compounds of the formula I in which one or more radicals mean R1 is H, $(C_1-C_{10})$-alkyl, $(C_3-C_{10})$-cycloalkyl, $(C_2-C_6)$-alkenyl, $(C_2-C_6)$-alkynyl or $(C_6-C_{10})$-aryl,
  wherein said $(C_1-C_{10})$-alkyl, $(C_3-C_{10})$-cycloalkyl, $(C_2-C_6)$-alkenyl, $(C_2-C_6)$-alkynyl and $(C_6-C_{10})$-aryl radicals are optionally substituted one or more times by F, Cl, Br, I, CN, $NO_2$, OH, $-CF_3$, $(C_1-C_6)$-alkyl, $(C_2-C_6)$-alkenyl, $(C_2-C_6)$-alkynyl, OR3, NR3R4, COR3, $CO_2R3$, CONR3R4, $(C_1-C_6)$-alkylene-OR3, $(C_1-C_6)$-alkylene-NR3R4, $(C_1-C_6)$-alkylene-SR3, alkylene-SOR3, alkylene-$SO_2$R3, $(C_1-C_6)$-alkylene-COR3, $(C_1-C_6)$-alkylene-CO$_2$R3, $(C_1-C_6)$-alkylene-CONR3R4, (C1–C6)-alkylene-O—P(O)(OR3)$_2$, SR3, SOR3, $SO_2$NR3R4, $SO_2$R3, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl or $(C_6-C_{10})$-aryl,
    wherein said $(C_6-C_{10})$-aryl is optionally substituted one or more times by F, Cl, Br, I, CN, $NO_2$, OH, $-CF_3$, $(C_1-C_6)$-alkyl, $(C_2-C_6)$-alkenyl, $(C_2-C_6)$-alkynyl, OR3, NR3R4, COR3, $CO_2R3$ or CONR3R4;

R2 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, CO2R3, CONR3R4 or CN,
  wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, $-CF_3$, $(C_2-C_6)$-alkenyl, $(C_2-C_6)$-alkynyl, OR3, OP(O)(OR3)$_2$, NR3R4, NR3CONR3R4, COR3, OCOR3, $CO_2R3$, CONR3R4, OCONR3R4, $(C_1-C_6)$-alkylene-OR3, $(C_1-C_6)$-alkylene-NR3R4, $(C_1-C_6)$-alkylene-NR3SO$_2$R4, $(C_1-C_6)$-alkylene-SR3, alkylene-SOR3, alkylene-$SO_2$R3, alkylene-$SO_2$NR3R4, $(C_1-C_6)$-alkylene-COR3, $(C_1-C_6)$-alkylene-CO$_2$R3, $(C_1-C_6)$-alkylene-CONR3R4, SR3, SOR3, $SO_2$R3, $SO_2$NR3R4, NR3SO$_2$R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl,
    wherein said $(C_6-C_{10})$-aryl is optionally substituted one or more times by F, Cl, Br, I, CN, $NO_2$, OH, $-CF_3$, $(C_1-C_6)$-alkyl, $(C_2-C_6)$-alkenyl, $(C_2-C_6)$-alkynyl, OR3, NR3R4, COR3, $CO_2R3$ or CONR3R4, and wherein said heterocyclyl is optionally substituted one or more times by F, Cl, Br, I, CN, NO$_2$, OH, —CF$_3$, (C$_1$–C$_6$)-alkyl, OR3, NR3R4, COR3, CO$_2$R3 or CONR3R4;

R3, R4 are each, independently of one another, H, (C$_1$–C$_6$)-alkyl, —CF$_3$, (C$_3$–C$_{10}$)-cycloalkyl, (C$_6$–C$_{10}$)-aryl, heterocyclyl, (C$_1$–C$_6$)-alkylene-CONR5R6, (C$_1$–C$_6$)-alkylene-CO$_2$R5, (C$_1$–C$_6$)-alkylene-COR5, (C$_1$–C$_6$)-alkylene-OR5, (C$_1$–C$_6$)-alkylene-NR5R6, (C$_1$–C$_6$)-alkylene-SR5, (C$_1$–C$_6$)-alkylene-SOR5, (C$_1$–C$_6$)-alkylene-SO$_2$R5, (C$_1$–C$_4$)-alkylene-(C$_6$–C$_{10}$)-aryl or (C$_1$–C$_4$)-alkylene-heterocyclyl;

R5, R6 are each, independently of one another, H, (C$_1$–C$_6$)-alkyl, (C$_3$–C$_{10}$)-cycloalkyl, (C$_1$–C$_6$)-alkylene-(C$_6$–C$_{10}$)-aryl, —(C$_6$–C$_{10}$)-aryl, heterocyclyl or (C$_1$–C$_6$)-alkylene-(C$_3$–C$_{10}$)-heterocyclyl;

X is S;

and pharmaceutically acceptable salts thereof.

Preference is further given to compounds of the formula I in which one or more radicals mean R1 is H;

R2 is H, (C$_1$–C$_{10}$)-alkyl, (C$_3$–C$_{10}$)-cycloalkyl, (C$_2$–C$_6$)-alkenyl, (C$_2$–C$_6$)-alkynyl, (C$_6$–C$_{10}$)-aryl, heterocyclyl, COR3, CO$_2$R3, CONR3R4 or CN, wherein said (C$_1$–C$_{10}$)-alkyl, (C$_3$–C$_{10}$)-cycloalkyl, (C$_2$–C$_6$)-alkenyl, (C$_2$–C$_6$)-alkynyl, (C$_6$–C$_{10}$)-aryl and heterocyclyl radicals are optionally substituted one or more times by F, Cl, Br, I, CN, NO$_2$, SH, SF$_5$, OH, (C$_1$–C$_6$)-alkyl, —CF$_3$, (C$_2$–C$_6$)-alkenyl, (C$_2$–C$_6$)-alkynyl, OR3, OP(O)(OR3)2, NR3R4, NR3CONR3R4, COR3, OCOR3, CO$_2$R3, CONR3R4, OCONR3R4, (C$_1$–C$_6$)-alkylene-OR3, (C$_1$–C$_6$)-alkylene-NR3R4, (C$_1$–C$_6$)-alkylene-NR3SO$_2$R4, (C$_1$–C$_6$)-alkylene-SR3, alkylene-SOR3, alkylene-SO$_2$R3, alkylene-S(O)$_2$NR3R4, (C$_1$–C$_6$)-alkylene-COR3, (C$_1$–C$_6$)-alkylene-CO$_2$R3, (C$_1$–C$_6$)-alkylene-CONR3R4, SR3, SOR3, SO$_2$R3, SO$_2$NR3R4, NR3SO$_2$R4, (C$_1$–C$_6$)-alkylene-(C$_3$–C$_{10}$)-cycloalkyl, (C$_1$–C$_6$)-alkylene-(C$_6$–C$_{10}$)-aryl, (C$_1$–C$_6$)-alkylene-heterocyclyl, (C$_3$–C$_{10}$)-cycloalkyl, (C$_6$–C$_{10}$)-aryl or heterocyclyl, wherein said (C$_6$–C$_{10}$)-aryl is optionally substituted one or more times by F, Cl, Br, I, CN, NO$_2$, OH, —CF$_3$, (C$_1$–C$_6$)-alkyl, (C$_2$–C$_6$)-alkenyl, (C$_2$–C$_6$)-alkynyl, OR3, NR3R4, COR3, CO$_2$R3 or CONR3R4, and wherein said heterocyclyl is optionally substituted one or more times by F, Cl, Br, I, CN, NO$_2$, OH, —CF$_3$, (C$_1$–C$_6$)-alkyl, OR3, NR3R4, COR3, CO$_2$R3 or CONR3R4;

R3, R4 are each, independently of one another, H, (C$_1$–C$_6$)-alkyl, —CF$_3$, (C$_3$–C$_{10}$)-cycloalkyl, (C$_6$–C$_{10}$)-aryl, heterocyclyl, (C$_1$–C$_6$)-alkylene-CONR5R6, (C$_1$–C$_6$)-alkylene-CO$_2$R5, (C$_1$–C$_6$)-alkylene-COR5, (C$_1$–C$_6$)-alkylene-OR5, (C$_1$–C$_6$)-alkylene-NR5R6, (C$_1$–C$_6$)-alkylene-SR5, (C$_1$–C$_6$)-alkylene-SOR5, (C$_1$–C$_6$)-alkylene-SO$_2$R5, (C$_1$–C$_4$)-alkylene-(C$_6$–C$_{10}$)-aryl or (C$_1$–C$_4$)-alkylene-heterocyclyl;

R5, R6 are each, independently of one another, H, (C$_1$–C$_6$)-alkyl, (C$_3$–C$_{10}$)-cycloalkyl, (C$_1$–C$_6$)-alkylene-(C$_6$–C$_{10}$)-aryl, —(C$_6$–C$_{10}$)-aryl, heterocyclyl or (C$_1$–C$_6$)-alkylene-(C$_3$–C$_{10}$)-heterocyclyl;

X is S;

and pharmaceutically acceptable salts thereof.

Preference is further given to compounds of the formula I in which one or more radicals mean R1 is H;

R2 is H, (C$_1$–C$_{10}$)-alkyl, (C$_3$–C$_{10}$)-cycloalkyl, (C$_2$–C$_6$)-alkenyl, (C$_2$–C$_6$)-alkynyl, (C$_6$–C$_{10}$)-aryl, a pyrrolidino, piperidino, hexamethyleneimino, morpholino, piperazino, thiomorpholino or homopiperazino radical, wherein said (C$_1$–C$_{10}$)-alkyl, (C$_3$–C$_{10}$)-cycloalkyl, (C$_2$–C$_6$)-alkenyl, (C$_2$–C$_6$)-alkynyl, (C$_6$–C$_{10}$)-aryl, a pyrrolidino, piperidino, hexamethyleneimino, morpholino, piperazino, thiomorpholino and homopiperazino radicals are optionally substituted one or more times by F, Cl, Br, CN, SF$_5$, OH, (C$_1$–C$_6$)-alkyl, —CF$_3$, (C$_2$–C$_6$)-alkenyl, OR3, NR3R4, NR3CONR3R4, COR3, OCOR3, CO$_2$R3, CONR3R4, OCONR3R4, (C$_1$–C$_6$)-alkylene-OR3, (C$_1$–C$_6$)-alkylene-NR3R4, (C$_1$–C$_6$)-alkylene-NR3SO$_2$R4, (C$_1$–C$_6$)-alkylene-SR3, alkylene-S(O)R3, alkylene-S(O)$_2$R3, alkylene-S(O)$_2$NR3R4, (C$_1$–C$_6$)-alkylene-COR3, (C$_1$–C$_6$)-alkylene-CO$_2$R3, (C$_1$–C$_6$)-alkylene-CONR3R4, SR3, SOR3, SO$_2$R3, SO$_2$NR3R4, NR3SO$_2$R4, (C$_1$–C$_6$)-alkylene-(C$_3$–C$_{10}$)-cycloalkyl, (C$_1$–C$_6$)-alkylene-(C$_6$–C$_{10}$)-aryl, (C$_1$–C$_6$)-alkylene-heterocyclyl, (C$_3$–C$_{10}$)-cycloalkyl, (C$_6$–C$_{10}$)-aryl or heterocyclyl, wherein said (C$_6$–C$_{10}$)-aryl is optionally substituted one or more times by F, Cl, Br, I, CN, OH, —CF$_3$, (C$_1$–C$_6$)-alkyl, OR3, NR3R4, COR3, CO2R3 or CONR3R4, and wherein said heterocyclyl is optionally substituted one or more times by F, Cl, Br, CN, NO$_2$, OH, —CF$_3$, (C$_1$–C$_6$)-alkyl, OR3, NR3R4, COR3, CO2R3 or CONR3R4;

R3, R4 are each, independently of one another, H, (C$_1$–C$_6$)-alkyl, —CF$_3$, (C$_3$–C$_{10}$)-cycloalkyl, (C$_6$–C$_{10}$)-aryl, heterocyclyl, (C$_1$–C$_6$)-alkylene-CONR5R6, (C$_1$–C$_6$)-alkylene-COOR5, (C$_1$–C$_6$)-alkylene-COR5, (C$_1$–C$_6$)-alkylene-OR5, (C$_1$–C$_6$)-alkylene-NR5R6, (C$_1$–C$_6$)-alkylene-SR5, (C$_1$–C$_6$)-alkylene-S(O)R5, (C$_1$–C$_6$)-alkylene-S(O)$_2$R5, (C$_1$–C$_4$)-alkylene-(C$_6$–C$_{10}$)-aryl or (C$_1$–C$_4$)-alkylene-heterocyclyl;

R5, R6 are each, independently of one another, H, (C$_1$–C$_6$)-alkyl, (C$_3$–C$_{10}$)-cycloalkyl, (C$_1$–C$_6$)-alkylene-(C$_6$–C$_{10}$)-aryl, —(C$_6$–C$_{10}$)-aryl, heterocyclyl or (C1–C6)-alkylene-(C$_3$–C$_{10}$)-heterocyclyl;

X is S;

and pharmaceutically acceptable salts thereof.

Preference is further given to compounds of the formula I in which one or more radicals mean R1 is H;

R2 is (C$_1$–C$_{10}$)-alkyl, (C$_3$–C$_{10}$)-cycloalkyl, phenyl, (C$_1$–C$_6$)-alkylene-phenyl, a pyrrolidino, piperidino, hexamethyleneimino, morpholino, piperazino, thiomorpholino or homopiperazino radical;

X is S;

and pharmaceutically acceptable salts thereof.

The invention relates to compounds of the formula I in the form of all their stereoisomeric forms such as racemates, racemic and enantiomeric mixtures and pure enantiomers and diastereomers.

Compounds of the formula I,

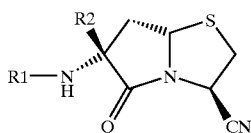

which have the indicated diastereomic form Ia are particularly preferred.

If radicals or substituents may occur more than once in the compounds of the formula I, they may all, independently of one another, have the stated meaning and be identical or different.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include prodrugs of the compounds of the invention, as described, for example, in H. Okada et al., Chem. Pharm. Bull. 1994, 42, 57–61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

An alkyl radical means a straight-chain or branched hydrocarbon chain having one or more carbons, such as, for example, methyl, ethyl, propyl, butyl, hexyl, isopropyl, neopentyl, tert-butyl, hexyl.

The alkyl radicals may be substituted one or more times by suitable groups such as, for example: F, Cl, Br, I, $CF_3$, $NO_2$, $N_3$, CN, COOH, COO($C_1$–$C_6$)alkyl, $CONH_2$, CONH($C_1$–$C_6$)alkyl, CON[($C_1$–$C_6$)alkyl]$_2$, cycloalkyl, ($C_2$–$C_6$)-alkenyl, ($C_2$–$C_6$)-alkynyl, aryl, heterocyclyl, O—($C_1$–$C_6$)-alkyl, O—COO, —($C_1$–$C_6$)-alkyl, O—CO—($C_1$–$C_6$)-alkyl, O—CO—($C_1$–$C_6$)-aryl, O—CO—($C_1$–$C_6$)-heterocyclyl; $PO_3H_2$, P(O)(Oalkyl)2, (C1–C6)-alkylene-P(O)(Oalkyl)2, O—P(O)(OH)$_2$, O—P(O)(Oalkyl)2, $SO_3H$, $SO_2$—$NH_2$, $SO_2NH$($C_1$–$C_6$)-alkyl, $SO_2N$[($C_1$–$C_6$)-alkyl]$_2$, S—($C_1$–$C_6$)-alkyl, S—$(CH_2)_n$-aryl, S—$(CH_2)_n$-heterocyclyl, SO—($C_1$–$C_6$)-alkyl, SO—$(CH_2)_n$-aryl, SO—$(CH_2)_n$-heterocyclyl, $SO_2$—($C_1$–$C_6$)-alkyl, $SO_2$—$(CH_2)_n$-aryl, $SO_2$—$(CH_2)_n$-heterocyclyl, $SO_2$—NH$(CH_2)_n$-aryl, $SO_2$—NH$(CH_2)_n$-heterocyclyl, $SO_2$—N[(($C_1$–$C_6$)-alkyl)$(CH_2)_n$-aryl], $SO_2$—N[(($C_1$–$C_6$)-alkyl)$(CH_2)_n$-heterocyclyl], $SO_2$—N(($(CH_2)_n$-aryl))$_2$, $SO_2$—N(($(CH_2)_n$-(heterocyclyl))$_2$, where n can be 0–6, and the aryl radical or heterocyclyl radical may be substituted up to three times by F, Cl, Br, OH, $CF_3$, $SF_5$, $NO_2$, CN, $OCF_3$, O—($C_1$–$C_6$)-alkyl, ($C_1$–$C_6$)-alkyl, $NH_2$; $C(NH)(NH_2)$, $NH_2$, NH—($C_1$–$C_6$)-alkyl, N(($C_1$–$C_6$)-alkyl)$_2$, NH($C_1$–$C_7$)-acyl, NH—CO—($C_1$–$C_6$)-alkyl, NH—COO—($C_1$–$C_6$)-alkyl, NH—CO-aryl, NH—CO-heterocyclyl, NH—COO-aryl, NH—COO-heterocyclyl, NH—CO—NH—($C_1$–$C_6$)-alkyl, NH—CO—NH-aryl, NH—CO—NH-heterocyclyl, N[($C_1$–$C_6$)-alkyl]-CO—($C_1$–$C_6$)-alkyl, N[($C_1$–$C_6$)-alkyl]-COO—($C_1$–$C_6$)-alkyl, N[($C_1$–$C_6$)-alkyl]-CO-aryl, N[($C_1$–$C_6$)-alkyl]-CO-heterocyclyl, N[($C_1$–$C_6$)-alkyl]-COO-aryl, N[($C_1$–$C_6$)-alkyl]-COO-heterocyclyl, N[($C_1$–$C_6$)-alkyl]-CO—NH—($C_1$–$C_6$)-alkyl), N[($C_1$–$C_6$)-alkyl]-CO—NH-aryl, N[($C_1$–$C_6$)-alkyl]-CO—NH-heterocyclyl, N[($C_1$–$C_6$)-alkyl]-CO—N(($C_1$–$C_6$)-alkyl)$_2$, N[($C_1$–$C_6$)-alkyl]-CO—N(($C_1$–$C_6$)-alkyl)-aryl, N[($C_1$–$C_6$)-alkyl]-CO—N(($C_1$–$C_6$)-alkyl)-heterocyclyl, N[($C_1$–$C_6$)-alkyl]-CO—N-(aryl)$_2$, N[($C_1$–$C_6$)-alkyl]-CO—N-(heterocyclyl)$_2$, N(aryl)-CO—($C_1$–$C_6$)-alkyl, N(heterocyclyl)-CO—($C_1$–$C_6$)-alkyl, N(aryl)-COO—($C_1$–$C_6$)-alkyl, N(heterocyclyl)-COO—($C_1$–$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$–$C_6$)-alkyl, N(heterocyclyl)-CO—NH—($C_1$–$C_6$)-alkyl, N(aryl)-CO—NH-aryl, N(heterocyclyl)-CO—NH-aryl, N(aryl)-CO—N(($C_1$–$C_6$)-alkyl)$_2$, N(heterocyclyl)-CO—N(($C_1$–$C_6$)-alkyl)$_2$, N(aryl)-CO—N[($C_1$–$C_6$)-alkyl]-aryl, N(heterocyclyl)-CO—N[($C_1$–$C_6$)-alkyl]-aryl, N(aryl)-CO—N-(aryl)$_2$, N(heterocyclyl)-CO—N-(aryl)$_2$, aryl, O—$(CH_2)_n$-aryl, O—$(CH_2)_n$-heterocyclyl, where n may be 0–6, where the aryl radical or heterocyclyl radical may be substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl, $SF_5$, $CONH_2$.

An alkenyl radical means a straight-chain or branched hydrocarbon chain having two or more carbons and one or more double bonds, such as, for example, vinyl, allyl, pentenyl. The alkenyl radicals may be substituted one or more times by suitable groups such as, for example: F, Cl, Br, I, $CF_3$, $NO_2$, $N_3$, CN, COOH, COO($C_1$–$C_6$)alkyl, $CONH_2$, CONH($C_1$–$C_6$)alkyl, CON[($C_1$–$C_6$)alkyl]$_2$, cycloalkyl, ($C_1$–$C_{10}$)-alkyl, ($C_2$–$C_6$)-alkynyl, aryl, heterocyclyl, O—($C_1$–$C_6$)-alkyl, O—CO—($C_1$–$C_6$)-alkyl, O—CO—($C_1$–$C_6$)-aryl, O—CO—($C_1$–$C_6$)-heterocyclyl,; $PO_3H_2$, P(O)(Oalkyl)2, (C1–C6)-alkylene-P(O)(Oalkyl)2, O—P(O)(OH)$_2$, O—P(O)(Oalkyl)2, $SO_3H$, $SO_2$—$NH_2$, $SO_2NH$($C_1$–$C_6$)-alkyl, $SO_2N$[($C_1$–$C_6$)-alkyl]$_2$, S—($C_1$–$C_6$)-alkyl, S—$(CH_2)_n$-aryl, S—$(CH_2)_n$-heterocyclyl, SO—($C_1$–$C_6$)-alkyl, SO—$(CH_2)_n$-aryl, SO—$(CH_2)_n$-heterocyclyl, $SO_2$—($C_1$–$C_6$)-alkyl, $SO_2$—$(CH_2)_n$-aryl, $SO_2$—$(CH_2)_n$-heterocyclyl, $SO_2$—NH$(CH_2)_n$-aryl, $SO_2$—

NH(CH$_2$)$_n$-heterocyclyl, SO$_2$—N((C$_1$–C$_6$)-alkyl)(CH$_2$)$_n$-aryl, SO$_2$—N((C$_1$–C$_6$)-alkyl)(CH$_2$)$_n$-heterocyclyl, SO$_2$—N((CH$_2$)$_n$-aryl)$_2$, SO$_2$—N((CH$_2$)$_n$-(heterocyclyl)$_2$ where n may be 0–6 and the aryl radical or heterocyclyl radical may be substituted up to twice by F, Cl, Br, OH, CF$_3$, SF$_5$, NO$_2$, CN, OCF$_3$, O—(C$_1$–C$_6$)-alkyl, (C$_1$–C$_6$)-alkyl, NH$_2$;

C(NH)(NH$_2$), NH$_2$, NH—(C$_1$–C$_6$)-alkyl, N((C$_1$–C$_6$)-alkyl)$_2$, NH(C$_1$–C$_7$)-acyl, NH—CO—(C$_1$–C$_6$)-alkyl, NH—COO—(C$_1$–C$_6$)-alkyl, NH—CO-aryl, NH—CO-heterocyclyl, NH—COO-aryl, NH—COO-heterocyclyl, NH—CO—NH—(C$_1$–C$_6$)-alkyl), NH—CO—NH-aryl, NH—CO—NH-heterocyclyl, N[(C$_1$–C$_6$)-alkyl]-CO—(C$_1$–C$_6$)-alkyl, N[(C$_1$–C$_6$)-alkyl]-COO—(C$_1$–C$_6$)-alkyl, N[(C$_1$–C$_6$)-alkyl]-CO-aryl, N[(C$_1$–C$_6$)-alkyl]-CO-heterocyclyl, N[(C$_1$–C$_6$)-alkyl]-COO-aryl, N[(C$_1$–C$_6$)-alkyl]-COO-heterocyclyl, N[(C$_1$–C$_6$)-alkyl]-CO—NH—(C$_1$–C$_6$)-alkyl), N[(C$_1$–C$_6$)-alkyl]-CO—NH-aryl, N[(C$_1$–C$_6$)-alkyl]-CO—NH-heterocyclyl, N[(C$_1$–C$_6$)-alkyl]-CO—N((C$_1$–C$_6$)-alkyl)$_2$, N[(C$_1$–C$_6$)-alkyl]-CO—N((C$_1$–C$_6$)-alkyl)-aryl, N[(C$_1$–C$_6$)-alkyl]-CO—N((C$_1$–C$_6$)-alkyl)-heterocyclyl, N[(C$_1$–C$_6$)-alkyl]-CO—N(aryl)$_2$, N[(C$_1$–C$_6$)-alkyl]-CO—N(heterocyclyl)$_2$, N(aryl)-CO—(C$_1$–C$_6$)-alkyl, N(heterocyclyl)-CO—(C$_1$–C$_6$)-alkyl, N(aryl)-COO—(C$_1$–C$_6$)-alkyl, N(heterocyclyl)-COO—(C$_1$–C$_6$)-alkyl, N(aryl)-CO-aryl, N(heterocyclyl)-CO-aryl, N(aryl)-COO-aryl, N(heterocyclyl)-COO-aryl, N(aryl)-CO—NH—(C$_1$–C$_6$)-alkyl, N(heterocyclyl)-CO—NH—(C$_1$–C$_6$)-alkyl, N(aryl)-CO—NH-aryl, N(heterocyclyl)-CO—NH-aryl, N(aryl)-CO—N((C$_1$–C$_6$)-alkyl)$_2$, N(heterocyclyl)-CO—N((C$_1$–C$_6$)-alkyl)$_2$, N(aryl)-CO—N[(C$_1$–C$_6$)-alkyl]-aryl, N(heterocyclyl)-CO—N[(C$_1$–C$_6$)-alkyl]-aryl, N(aryl)-CO—N(aryl)$_2$, N(heterocyclyl)-CO—N(aryl)$_2$, aryl, O—(CH$_2$)$_n$-aryl, O—(CH$_2$)$_n$-heterocyclyl, where n may be 0–6, where the aryl radical or heterocyclyl radical may be substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SF$_5$, SO$_2$—CH$_3$, COOH, COO—(C$_1$–C$_6$)-alkyl, CONH$_2$.

An alkynyl radical means a straight-chain or branched hydrocarbon chain having two or more carbons and one or more triple bonds, such as, for example, ethynyl, propynyl, hexynyl.

The alkynyl radicals may be substituted one or more times by suitable groups such as, for example: F, Cl, Br, I, CF$_3$, NO$_2$, N$_3$, CN, COOH, COO(C$_1$–C$_6$)alkyl, CONH$_2$, CONH(C$_1$–C$_6$)alkyl, CON[(C$_1$–C$_6$)alkyl]$_2$, cycloalkyl, (C$_2$–C$_6$)-alkenyl, (C$_1$–C$_{10}$)-alkyl, O—(C$_1$–C$_6$)-alkyl, O—CO—(C$_1$–C$_6$)-alkyl, O—CO—(C$_1$–C$_6$)-aryl, O—CO—(C$_1$–C$_6$)-heterocyclyl;

PO$_3$H$_2$, P(O)(Oalkyl)2, (C1–C6)-alkylene-P(O)(Oalkyl)2, O—P(O)(OH)$_2$, O—P(O)(Oalkyl)2, SO$_3$H, SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-aryl, S—(CH$_2$)$_n$-heterocyclyl, SO—(C$_1$–C$_6$)-alkyl, SO—(CH$_2$)$_n$-aryl, SO—(CH$_2$)$_n$-heterocyclyl, SO$_2$—(C$_1$–C$_6$)-alkyl, SO$_2$—(CH$_2$)$_n$-aryl, SO$_2$—(CH$_2$)$_n$-heterocyclyl, SO$_2$—NH(CH$_2$)$_n$-aryl, SO$_2$—NH(CH$_2$)$_n$-heterocyclyl, SO$_2$—N((C$_1$–C$_6$)-alkyl)(CH$_2$)$_n$-aryl, SO$_2$—N((C$_1$–C$_6$)-alkyl)(CH$_2$)$_n$-heterocyclyl, SO$_2$—N((CH$_2$)$_n$-aryl)$_2$, SO$_2$—N((CH$_2$)$_n$-(heterocyclyl)$_2$ where n may be 0–6 and the aryl radical or heterocyclyl radical may be substituted up to twice by F, Cl, Br, OH, CF$_3$, NO$_2$, SF$_5$, CN, OCF$_3$, O—(C$_1$–C$_6$)-alkyl, (C$_1$–C$_6$)-alkyl, NH$_2$;

C(NH)(NH$_2$), NH$_2$, NH—(C$_1$–C$_6$)-alkyl, N((C$_1$–C$_6$)-alkyl)$_2$, NH(C$_1$–C$_7$)-acyl, NH—CO—(C$_1$–C$_6$)-alkyl, NH—COO—(C$_1$–C$_6$)-alkyl, NH—CO-aryl, NH—CO-heterocyclyl, NH—COO-aryl, NH—COO-heterocyclyl, NH—CO—NH—(C$_1$–C$_6$)-alkyl), NH—CO—NH-aryl, NH—CO—NH-heterocyclyl, N[(C$_1$–C$_6$)-alkyl]-CO—(C$_1$–C$_6$)-alkyl, N[(C$_1$–C$_6$)-alkyl]-COO—(C$_1$–C$_6$)-alkyl, N[(C$_1$–C$_6$)-alkyl]-CO-aryl, N[(C$_1$–C$_6$)-alkyl]-CO-heterocyclyl, N[(C$_1$–C$_6$)-alkyl]-COO-aryl, N[(C$_1$–C$_6$)-alkyl]-COO-heterocyclyl, N[(C$_1$–C$_6$)-alkyl]-CO—NH—(C$_1$–C$_6$)-alkyl), N[(C$_1$–C$_6$)-alkyl]-CO—NH-aryl, N[(C$_1$–C$_6$)-alkyl]-CO—NH-heterocyclyl, N[(C$_1$–C$_6$)-alkyl]-CO—N((C$_1$–C$_6$)-alkyl)$_2$, N[(C$_1$–C$_6$)-alkyl]-CO—N((C$_1$–C$_6$)-alkyl)-aryl, N[(C$_1$–C$_6$)-alkyl]-CO—N((C$_1$–C$_6$)-alkyl)-heterocyclyl, N[(C$_1$–C$_6$)-alkyl]-CO—N(aryl)$_2$, N[(C$_1$–C$_6$)-alkyl]-CO—N(heterocyclyl)$_2$, N(aryl)-CO—(C$_1$–C$_6$)-alkyl, N(heterocyclyl)-CO—(C$_1$–C$_6$)-alkyl, N(aryl)-COO—(C$_1$–C$_6$)-alkyl, N(heterocyclyl)-COO—(C$_1$–C$_6$)-alkyl, N(aryl)-CO-aryl, N(heterocyclyl)-CO-aryl, N(aryl)-COO-aryl, N(heterocyclyl)-COO-aryl, N(aryl)-CO—NH—(C$_1$–C$_6$)-alkyl, N(heterocyclyl)-CO—NH—(C$_1$–C$_6$)-alkyl, N(aryl)-CO—NH-aryl, N(heterocyclyl)-CO—NH-aryl, N(aryl)-CO—N((C$_1$–C$_6$)-alkyl)$_2$, N(heterocyclyl)-CO—N((C$_1$–C$_6$)-alkyl)$_2$, N(aryl)-CO—N[(C$_1$–C$_6$)-alkyl]-aryl, N(heterocyclyl)-CO—N[(C$_1$–C$_6$)-alkyl]-aryl, N(aryl)-CO—N(aryl)$_2$, N(heterocyclyl)-CO—N(aryl)$_2$, aryl, O—(CH$_2$)$_n$-aryl, O—(CH$_2$)$_n$-heterocyclyl, where n may be 0–6, where the aryl radical or heterocyclyl radical may be substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SF$_5$, SO$_2$—CH$_3$, COOH, COO—(C$_1$–C$_6$)-alkyl, CONH$_2$.

An aryl radical means a phenyl, naphthyl, biphenyl, tetrahydronaphthyl, alpha- or beta-tetralon-, indanyl- or indan-1-on-yl radical.

The aryl radicals may be substituted one or more times by suitable groups such as, for example: F, Cl, Br, I, CF$_3$, NO$_2$, SF$_5$, N$_3$, CN, COOH, COO(C$_1$–C$_6$)alkyl, CONH$_2$, CONH(C$_1$–C$_6$)alkyl, CON[(C$_1$–C$_6$)alkyl]$_2$, cycloalkyl, (C$_1$–C$_{10}$)-alkyl, (C$_2$–C$_6$)-alkenyl, (C$_2$–C$_6$)-alkynyl, O—(C$_1$–C$_6$)-alkyl, O—CO—(C$_1$–C$_6$)-alkyl, O—CO—(C$_1$–C$_6$)-aryl, O—CO—(C$_1$–C$_6$)-heterocyclyl;

PO$_3$H$_2$, P(O)(Oalkyl)2, (C1–C6)-alkylene-P(O)(Oalkyl)2, O—P(O)(OH)$_2$, O—P(O)(Oalkyl)2, SO$_3$H, SO$_2$—NH$_2$, SO$_2$NH(C$_1$–C$_6$)-alkyl, SO$_2$N[(C$_1$–C$_6$)-alkyl]$_2$, S—(C$_1$–C$_6$)-alkyl, S—(CH$_2$)$_n$-aryl, S—(CH$_2$)$_n$-heterocyclyl, SO—(C$_1$–C$_6$)-alkyl, SO—(CH$_2$)$_n$-aryl, SO—(CH$_2$)$_n$-heterocyclyl, SO$_2$—(C$_1$–C$_6$)-alkyl, SO$_2$—(CH$_2$)$_n$-aryl, SO$_2$—(CH$_2$)$_n$-heterocyclyl, SO$_2$—NH(CH$_2$)$_n$-aryl, SO$_2$—NH(CH$_2$)$_n$-heterocyclyl, SO$_2$—N((C$_1$–C$_6$)-alkyl)(CH$_2$)$_n$-aryl, SO$_2$—N((C$_1$–C$_6$)-alkyl)(CH$_2$)$_n$-heterocyclyl, SO$_2$—N((CH$_2$)$_n$-aryl)$_2$, SO$_2$—N((CH$_2$)$_n$-(heterocyclyl)$_2$ where n may be 0–6 and the aryl radical or heterocyclyl radical may be substituted up to twice by F, Cl, Br, OH, CF$_3$, NO$_2$, SF$_5$, CN, OCF$_3$, O—(C$_1$–C$_6$)-alkyl, (C$_1$–C$_6$)-alkyl, NH$_2$;

C(NH)(NH$_2$), NH$_2$, NH—(C$_1$–C$_6$)-alkyl, N((C$_1$–C$_6$)-alkyl)$_2$, NH(C$_1$–C$_7$)-acyl, NH—CO—(C$_1$–C$_6$)-alkyl, NH—COO—(C$_1$–C$_6$)-alkyl, NH—CO-aryl, NH—CO-heterocyclyl, NH—COO-aryl, NH—COO-heterocyclyl, NH—CO—NH—(C$_1$–C$_6$)-alkyl), NH—CO—NH-aryl, NH—CO—NH-heterocyclyl, N[(C$_1$–C$_6$)-alkyl]-CO—(C$_1$–C$_6$)-alkyl, N[(C$_1$–C$_6$)-alkyl]-COO—(C$_1$–C$_6$)-alkyl, N[(C$_1$–C$_6$)-alkyl]-CO-aryl, N[(C$_1$–C$_6$)-alkyl]-CO-heterocyclyl, N[(C$_1$–C$_6$)-alkyl]-COO-aryl, N[(C$_1$–C$_6$)-alkyl]-COO-heterocyclyl, N[(C$_1$–C$_6$)-alkyl]-CO—NH—(C$_1$–C$_6$)-alkyl), N[(C$_1$–C$_6$)-alkyl]-CO—NH-aryl, N[(C$_1$–C$_6$)-alkyl]-CO—NH-heterocyclyl, N[(C$_1$–C$_6$)-alkyl]-CO—N((C$_1$–C$_6$)-alkyl)$_2$, N[(C$_1$–C$_6$)-alkyl]-CO—N((C$_1$–C$_6$)-alkyl)-aryl, N[(C$_1$–C$_6$)-alkyl]-CO—N((C$_1$–C$_6$)-alkyl)-heterocyclyl, N[(C$_1$–C$_6$)-alkyl]-CO—N(aryl)$_2$, N[(C$_1$–C$_6$)-alkyl]-CO—N(heterocyclyl)$_2$, N(aryl)-CO—(C$_1$–C$_6$)-alkyl, N(heterocyclyl)-CO—(C$_1$–C$_6$)-alkyl, N(aryl)-COO—(C$_1$–C$_6$)-alkyl, N(heterocyclyl)-COO—($C_1$–$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$–$C_6$)-alkyl, N(heterocyclyl)-CO—NH—($C_1$–$C_6$)-alkyl, N(aryl)-CO—NH-aryl, N(heterocyclyl)-CO—NH-aryl, N(aryl)-CO—N(($C_1$–$C_6$)-alkyl)$_2$, N(heterocyclyl)-CO—N(($C_1$–$C_6$)-alkyl)$_2$, N(aryl)-CO—N[($C_1$–$C_6$)-alkyl]-aryl, N(heterocyclyl)-CO—N[($C_1$–$C_6$)-alkyl]-aryl, N(aryl)-CO—N(aryl)$_2$, N(heterocyclyl)-CO—N(aryl)$_2$, aryl, O—($CH_2$)$_n$-aryl, O—($CH_2$)$_n$-heterocyclyl, where n may be 0–6, where the aryl radical or heterocyclyl radical may be substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl)$_2$, $SF_5$, $SO_2$—$CH_3$, COOH, COO—($C_1$–$C_6$)-alkyl, $CONH_2$.

A cycloalkyl radical means a ring system which comprises one or more rings and which is saturated or partially unsaturated (with one or two double bonds), and which is composed exclusively of carbon atoms, for example, cyclopropyl, cyclopentyl, cyclopentenyl, cyclohexyl or adamantyl.

The cycloalkyl radicals may be substituted one or more times by suitable groups such as, for example: F, Cl, Br, I, $CF_3$, $NO_2$, $N_3$, CN, COOH, COO($C_1$–$C_6$)alkyl, $CONH_2$, CONH($C_1$–$C_6$)alkyl, CON[($C_1$–$C_6$)alkyl]$_2$, cycloalkyl, ($C_1$–$C_{10}$)-alkyl, ($C_2$–$C_6$)-alkenyl, ($C_2$–$C_6$)-alkynyl, O—($C_1$–$C_6$)-alkyl, O—CO—($C_1$–$C_6$)-alkyl, O—CO—($C_1$–$C_6$)-aryl, O—CO—($C_1$–$C_6$)-heterocyclyl;

$PO_3H_2$, P(O)(Oalkyl)2, (C1–C6)-alkylene-P(O)(Oalkyl)2, O—P(O)(OH)$_2$, O—P(O)(Oalkyl)2, $SO_3H$, $SO_2$—$NH_2$, $SO_2NH$($C_1$–$C_6$)-alkyl, $SO_2N$[($C_1$–$C_6$)-alkyl]$_2$, S—($C_1$–$C_6$)alkyl, S—($CH_2$)$_n$-aryl, S—($CH_2$)$_n$-heterocyclyl, SO—($C_1$–$C_6$)-alkyl, SO—($CH_2$)$_n$-aryl, SO—($CH_2$)$_n$-heterocyclyl, $SO_2$—($C_1$–$C_6$)-alkyl, $SO_2$—($CH_2$)$_n$-aryl, $SO_2$—($CH_2$)$_n$-heterocyclyl, $SO_2$—NH($CH_2$)$_n$-aryl, $SO_2$—NH($CH_2$)$_n$-heterocyclyl, $SO_2$—N(($C_1$–$C_6$)-alkyl)($CH_2$)$_n$-aryl, $SO_2$—N(($C_1$–$C_6$)-alkyl)($CH_2$)$_n$-heterocyclyl, $SO_2$—N(($CH_2$)$_n$-aryl)$_2$, $SO_2$—N(($CH_2$)$_n$-(heterocyclyl)$_2$ where n may be 0–6and the aryl radical or heterocyclyl radical may be substituted up to twice by F, Cl, Br, OH, $CF_3$, $SF_5$, $NO_2$, CN, $OCF_3$, O—($C_1$–$C_6$)-alkyl, ($C_1$–$C_6$)-alkyl, $NH_2$;

C(NH)($NH_2$), $NH_2$, NH—($C_1$–$C_6$)-alkyl, N(($C_1$–$C_6$)-alkyl)$_2$, NH($C_1$–$C_7$)-acyl, NH—CO—($C_1$–$C_6$)-alkyl, NH—COO—($C_1$–$C_6$)-alkyl, NH—CO-aryl, NH—CO-heterocyclyl, NH—COO-aryl, NH—COO-heterocyclyl, NH—CO—NH—($C_1$–$C_6$)-alkyl), NH—CO—NH-aryl, NH—CO—NH-heterocyclyl, N[($C_1$–$C_6$)-alkyl]-CO—($C_1$–$C_6$)-alkyl, N[($C_1$–$C_6$)-alkyl]-COO—($C_1$–$C_6$)-alkyl, N[($C_1$–$C_6$)-alkyl]-CO-aryl, N[($C_1$–$C_6$)-alkyl]-CO-heterocyclyl, N[($C_1$–$C_6$)-alkyl]-COO-aryl, N[($C_1$–$C_6$)-alkyl]-COO-heterocyclyl, N[($C_1$–$C_6$)-alkyl]-CO—NH—($C_1$–$C_6$)-alkyl), N[($C_1$–$C_6$)-alkyl]-CO—NH-aryl, N[($C_1$–$C_6$)-alkyl]-CO—NH-heterocyclyl, N[($C_1$–$C_6$)-alkyl]-CO—N(($C_1$–$C_6$)-alkyl)$_2$, N[($C_1$–$C_6$)-alkyl]-CO—N(($C_1$–$C_6$)-alkyl)-aryl, N[($C_1$–$C_6$)-alkyl]-CO—N($C_1$–$C_6$)-alkyl)-heterocyclyl, N[($C_1$–$C_6$)-alkyl]-CO—N(aryl)$_2$, N[($C_1$–$C_6$)-alkyl]-CO—N(heterocyclyl)$_2$, N(aryl)-CO—($C_1$–$C_6$)-alkyl, N(heterocyclyl)-CO—($C_1$–$C_6$)-alkyl, N(aryl)-COO—($C_1$–$C_6$)-alkyl, N(heterocyclyl)-COO—($C_1$–$C_6$)-alkyl, N(aryl)-CO-aryl, N(heterocyclyl)-CO-aryl, N(aryl)-COO-aryl, N(heterocyclyl)-COO-aryl, N(aryl)-CO—NH—($C_1$–$C_6$)-alkyl, N(heterocyclyl)-CO—NH—($C_1$–$C_6$)-alkyl, N(aryl)-CO—NH-aryl, N(heterocyclyl)-CO—NH-aryl, N(aryl)-CO—N(($C_1$–$C_6$)-alkyl)$_2$, N(heterocyclyl)-CO—N(($C_1$–$C_6$)-alkyl)$_2$, N(aryl)-CO—N[($C_1$–$C_6$)-alkyl]-aryl, N(heterocyclyl)-CO—N[($C_1$–$C_6$)-alkyl]-aryl, N(aryl)-CO—N(aryl)$_2$, N(heterocyclyl)-CO—N(aryl)$_2$, aryl, O—($CH_2$)$_n$-aryl, O—($CH_2$)$_n$-heterocyclyl, where n may be 0–6, where the aryl radical or heterocyclyl radical may be substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SF_5$, $SO_2$—$CH_3$, COOH, COO—($C_1$–$C_6$)-alkyl, $CONH_2$.

Heterocyclyl or heterocyclic radical means rings or ring systems which, apart from carbon, also comprise heteroatoms such as, for example, nitrogen, oxygen or sulfur. Ring systems in which the heterocycle or heterocyclic radical is fused to benzene nuclei are also included in this definition.

Suitable heterocyclyl radicals or "heterocyclic radicals" are acridinyl, benzimidazolyl, benzofuryl, benzothienyl, benzothiophenyl, benzoxazolyl, benzthiazolyl, benztriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl, aziridinyl, azetininyl, azepanyl, azocanyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of these compounds, that is to say, for example, 1-oxy-2-, 3- or 4-pyridyl.

Also included are derivatives of these heterocycles which are benzo-fused one or more times.

The heterocyclic rings or heterocyclic radicals may be substituted one or more times by suitable groups such as, for example: F, Cl, Br, I, $CF_3$, $NO_2$, $N_3$, CN, COOH, COO($C_1$–$C_6$)alkyl, $CONH_2$, CONH($C_1$–$C_6$)alkyl, CON[($C_1$–$C_6$)alkyl]$_2$, cycloalkyl, ($C_1$–$C_{10}$)-alkyl, ($C_2$–$C_6$)-alkenyl, ($C_2$–$C_6$)-alkynyl, O—($C_1$–$C_6$)-alkyl, O—CO—($C_1$–$C_6$)-alkyl, O—CO—($C_1$–$C_6$)-aryl, O—CO—($C_1$–$C_6$)-heterocyclyl;

$PO_3H_2$, P(O)(Oalkyl)2, (C1–C6)-alkylene-P(O)(Oalkyl)2, O—P(O)(OH)$_2$, O—P(O)(Oalkyl)2, $SO_3H$, $SO_2$—$NH_2$, $SO_2NH$($C_1$–$C_6$)-alkyl, $SO_2N$[($C_1$–$C_6$)-alkyl]$_2$, S—($C_1$–$C_6$)-alkyl, S—($CH_2$)$_n$-aryl, S—($CH_2$)$_n$-heterocyclyl, SO—($C_1$–$C_6$)-alkyl, SO—($CH_2$)$_n$-aryl, SO—($CH_2$)$_n$-heterocyclyl, $SO_2$—($C_1$–$C_6$)-alkyl, $SO_2$—($CH_2$)$_n$-aryl, $SO_2$—($CH_2$)$_n$-heterocyclyl, $SO_2$—NH($CH_2$)$_n$-aryl, $SO_2$—NH($CH_2$)$_n$-heterocyclyl, $SO_2$—N($C_1$–$C_6$)-alkyl)($CH_2$)$_n$-aryl, $SO_2$—N(($C_1$–$C_6$)-alkyl)($CH_2$)$_n$-heterocyclyl, $SO_2$—N(($CH_2$)$_n$-aryl)$_2$, $SO_2$—N(($CH_2$)$_n$-(heterocyclyl)$_2$ where n can be 0–6, and the aryl radical or heterocyclyl radical may be substituted up to twice by F, Cl, Br, OH, $CF_3$, $SF_5$, $NO_2$, CN, $OCF_3$, O—($C_1$–$C_6$)-alkyl, ($C_1$–$C_6$)-alkyl, $NH_2$;

C(NH)(NH$_2$), NH$_2$, NH—(C$_1$-C$_6$)-alkyl, N((C$_1$-C$_6$)-alkyl)$_2$, NH(C$_1$-C$_7$)-acyl, NH—CO—(C$_1$-C$_6$)-alkyl, NH—COO—(C$_1$-C$_6$)-alkyl, NH—CO-aryl, NH—CO-heterocyclyl, NH—COO-aryl, NH—COO-heterocyclyl, NH—CO—NH—(C$_1$-C$_6$)-alkyl), NH—CO—NH-aryl, NH—CO—NH-heterocyclyl, N[(C$_1$-C$_6$)-alkyl]-CO—(C$_1$-C$_6$)-alkyl, N[(C$_1$-C$_6$)-alkyl]-COO—(C$_1$-C$_6$)-alkyl, N[(C$_1$-C$_6$)-alkyl]-CO-aryl, N[(C$_1$-C$_6$)-alkyl]-CO-heterocyclyl, N[(C$_1$-C$_6$)-alkyl]-COO-aryl, N[(C$_1$-C$_6$)-alkyl]-COO-heterocyclyl, N[(C$_1$-C$_6$)-alkyl]-CO—NH—(C$_1$-C$_6$)-alkyl), N[(C$_1$-C$_6$)-alkyl]-CO—NH-aryl, N[(C$_1$-C$_6$)-alkyl]-CO—NH-heterocyclyl, N[(C$_1$-C$_6$)-alkyl]-CO—N((C$_1$-C$_6$)-alkyl)$_2$, N[(C$_1$-C$_6$)-alkyl]-CO—N((C$_1$-C$_6$)-alkyl)-aryl, N[(C$_1$-C$_6$)-alkyl]-CO—N((C$_1$-C$_6$)-alkyl)-heterocyclyl, N[(C$_1$-C$_6$)-alkyl]-CO—N(aryl)$_2$, N[(C$_1$-C$_6$)-alkyl]-CO—N(heterocyclyl)$_2$, N(aryl)-CO—(C$_1$-C$_6$)-alkyl, N(heterocyclyl)-CO—(C$_1$-C$_6$)-alkyl, N(aryl)-COO—(C$_1$-C$_6$)-alkyl, N(heterocyclyl)-COO—(C$_1$-C$_6$)-alkyl, N(aryl)-CO-aryl, N(heterocyclyl)-CO-aryl, N(aryl)-COO-aryl, N(heterocyclyl)-COO-aryl, N(aryl)-CO—NH—(C$_1$-C$_6$)-alkyl, N(heterocyclyl)-CO—NH—(C$_1$-C$_6$)-alkyl, N(aryl)-CO—NH-aryl, N(heterocyclyl)-CO—NH-aryl, N(aryl)-CO—N((C$_1$-C$_6$)-alkyl)$_2$, N(heterocyclyl)-CO—N((C$_1$-C$_6$)-alkyl)$_2$, N(aryl)-CO—N[(C$_1$-C$_6$)-alkyl]-aryl, N(heterocyclyl)-CO—N[(C$_1$-C$_6$)-alkyl]-aryl, N(aryl)-CO—N(aryl)$_2$, N(heterocyclyl)-CO—N(aryl)$_2$, aryl, O—(CH$_2$)$_n$-aryl, O—(CH$_2$)$_n$-heterocyclyl, where n may be 0–6, where the aryl radical or heterocyclyl radical may be substituted one to 3 times by F, Cl, Br, I, OH, CF$_3$, NO$_2$, CN, OCF$_3$, SF$_5$, O—(C$_1$-C$_6$)-alkyl, (C$_1$-C$_6$)-alkyl, NH$_2$, NH(C$_1$-C$_6$)-alkyl, N((C$_1$-C$_6$)-alkyl)$_2$, SF$_5$, SO$_2$—CH$_3$, COOH, COO—(C$_1$-C$_6$)-alkyl, CONH$_2$.

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The compounds of the formula 1 can be prepared by methods known per se. Thus, it is possible starting from commercially available D-allylglycine 2 by protection of the amino group with usual protective groups such as Boc to 3, oxidation of the allyl group with ozone or osmium tetroxide/sodium periodate to the cyclic aldehyde derivative 4, reaction with cysteine derivatives such as, for example, the methyl ester to 5, cyclization with usual, acid activating, reagents such as DCC or chloromethylpyridinium iodide, ammonolysis of the resulting bicyclic thiazolidine ester 6 with methanolic ammonia solution, conversion of the resulting amide 7 into the nitrile 8 and derivatization of the amine by usual methods such as alkylation with alkyl halides or reductive alkylation with aldehydes or ketones to the nitriles 9. On the other hand, it is possible by using L-allylglycine as commercially available starting compound to prepare stereoisomeric forms of the derivatives 8 and 9. The diastereoisomeric mixtures 5 which are obtained on cyclization with cysteine derivatives by usual methods can be fractionated into the individual diastereomers by known methods such as, for example, by column chromatography or by recrystallization from a suitable solvent. The stereoisomeric forms can, however, also be separated and purified by usual methods at a later stage of the synthesis.

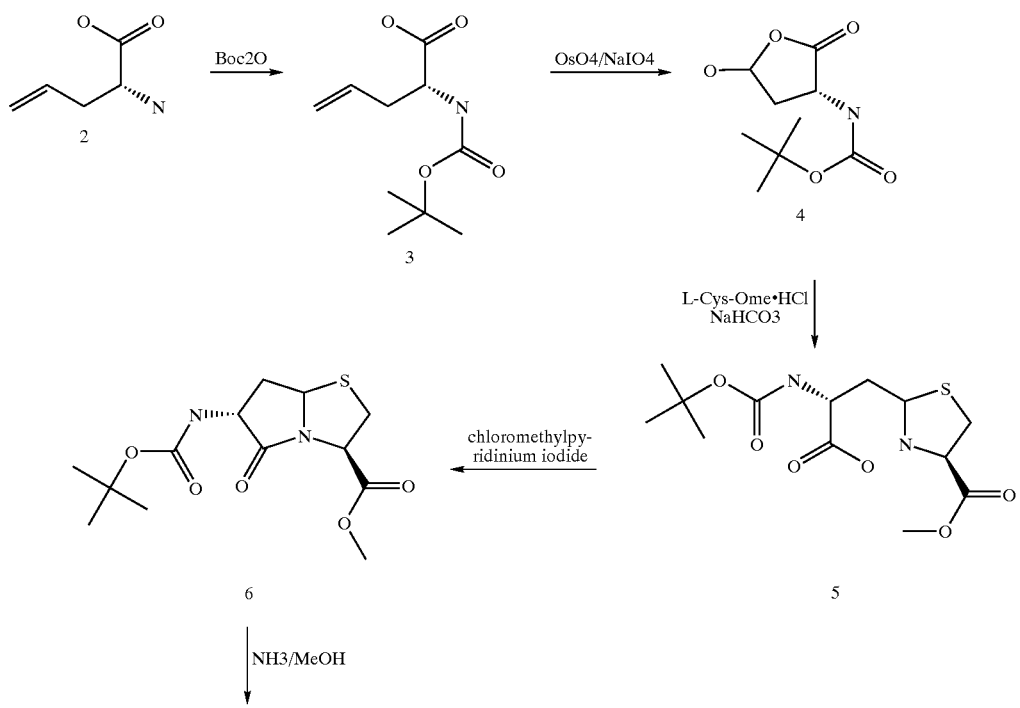

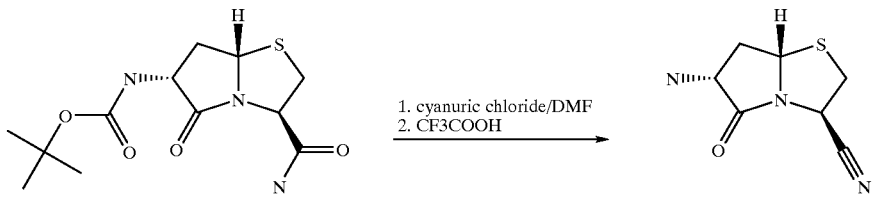

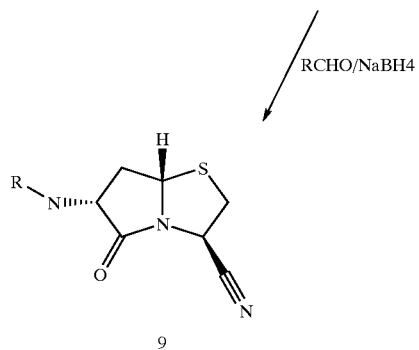

A further method for preparing the compounds of the invention of the formula 1 consists of a conversion, known per se, of commercially available acids 10, in which R2 cannot be hydrogen, into the oxazolidones 11 by the action of pivalaldehyde and allyl chloroformate. It is then possible to prepare from 11 by reaction with strong bases such as, for example, potassium bistrimethylsilylamide and alkylation with allyl bromide, with subsequent removal of the protective groups and ring opening under suitable conditions, the amino acids 12 (Heterocycles 34 (5), 1992 903–906) from which the aldehydes 15 are obtainable, after introduction of N-protective groups such as, for example, the BOC group to give 13 and esterification to give 14 for example with diazomethane or trimethylsilyldiazomethane, by oxidation with osmium tetroxide and sodium periodate. It is possible by heating these aldehydes with L-cysteine in pyridine to obtain the bicyclic derivatives 16 and, from them, by known methods by esterification the substances 17, and by ammonolysis the amides 18. Conversion of the amide 18 into a nitrile 19 with, for example, trifluoroacetic anhydride or cyanuric chloride and elimination of the protective group by known processes leads to the substances 20 of the invention, which can be isolated where appropriate as salts or free bases.

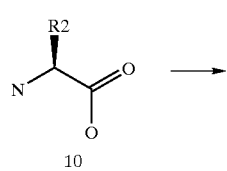

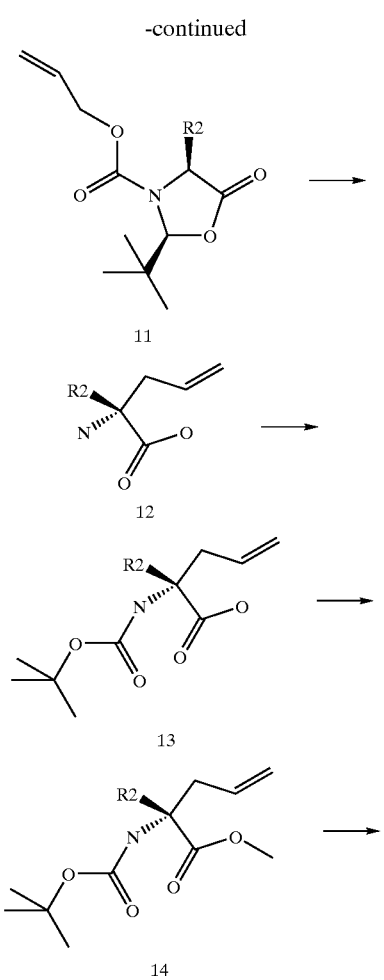

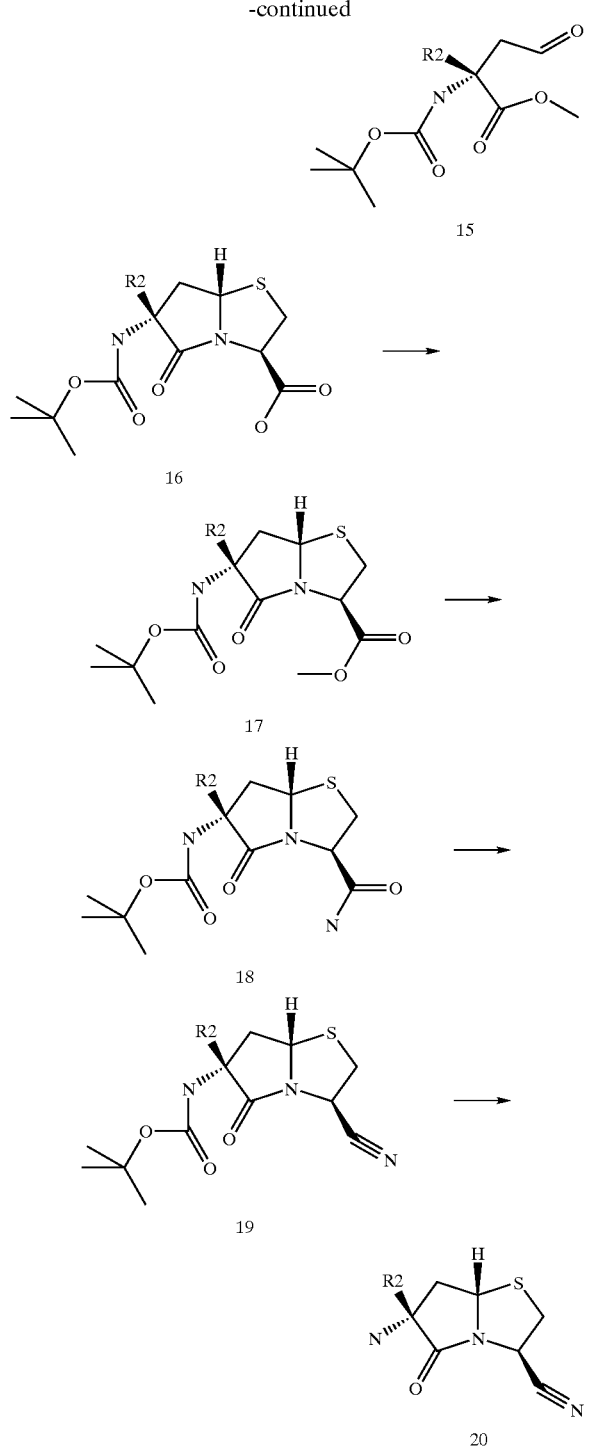

group, e.g. Cl, Br, I, mesyl, tosyl, triflate) to give the compound 23. Cleavage with alkali metals (e.g. sodium) in liquid ammonia affords compound 24. Oxidation with osmium tetroxide/sodium periodate or ozone then results in the cyclic aldehyde derivative 25. This is followed by reaction with L-cysteine derivatives (e.g. L-cysteine methyl ester hydrochloride) in the presence of a base (e.g. triethylamine or Hünig's base), resulting in a thiazolidine intermediate which cyclizes in the presence of an acid activating reagent such as, for example, a carbodiimide (e.g. N'-(3-dimethylaminopropyl)-N-ethylcarbodiimide hydrochloride) to give the two diastereomeric thiazolidides 26 and 27. After separation of the diastereomers using suitable methods, such as by recrystallization or chromatographic methods, compound 26 is converted with ammonia into the amide 28. Reaction to give the nitrile 29 by usual methods (e.g. trifluoroacetic anhydride and triethylamine, or cyanuric chloride) and elimination of the Boc group under acidic conditions (e.g. trifluoroacetic acid in the presence of thioanisole) affords the compound 30 which can then be converted as mentioned above into the substances 31.

Diastereomers of these compounds can be prepared correspondingly starting from other enantiomers of the starting compound 21, or by further reaction of the diastereomers 27 to give the stereoisomeric derivatives analogous to formula 30 and 31.

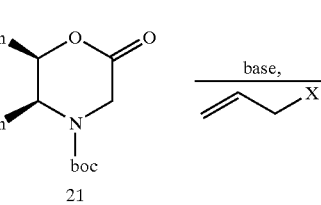

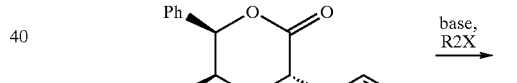

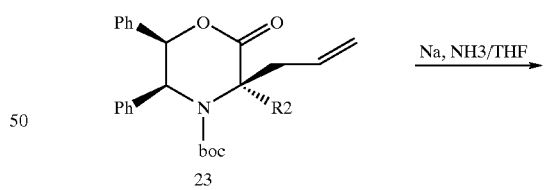

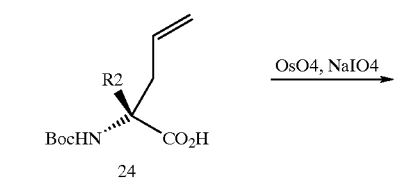

A further possibility for producing compounds of the general formula 1 consists in converting the commercially available compound 21 by deprotonation with a strong base (e.g. potassium hexamethyldisilazide (KHMDS)) and alkylation with an allyl derivative (e.g. allyl bromide) into the compound 22 (*Synlett* 1992, 249–251). This is followed by deprotonation again with a strong base (e.g. sodium hexamethyldisilazide (NaHMDS) in the presence of 15-crown-5) and then reaction with an alkylating agent R2X (X=leaving

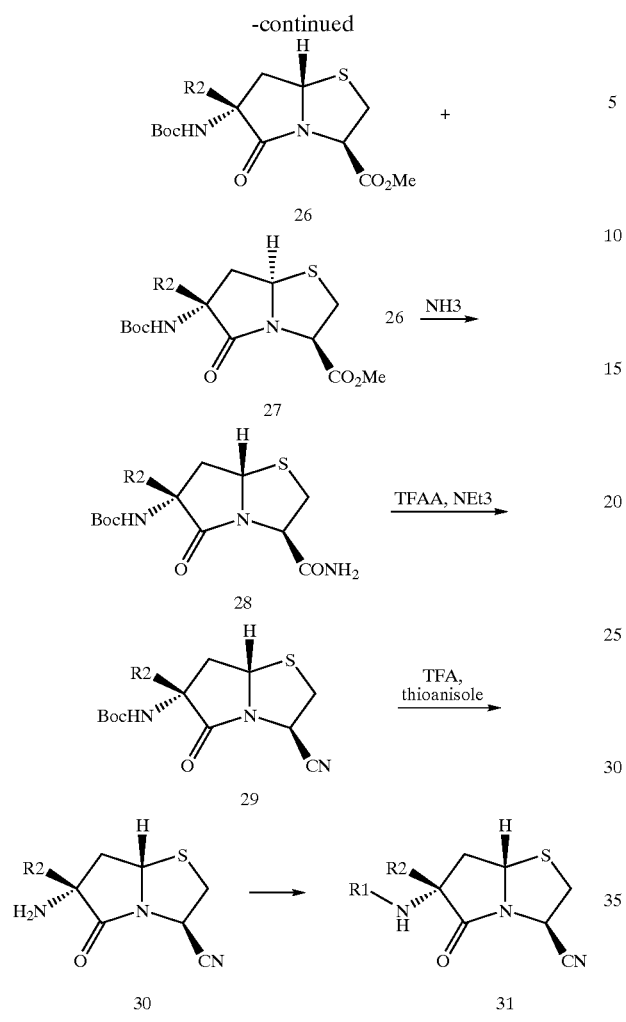

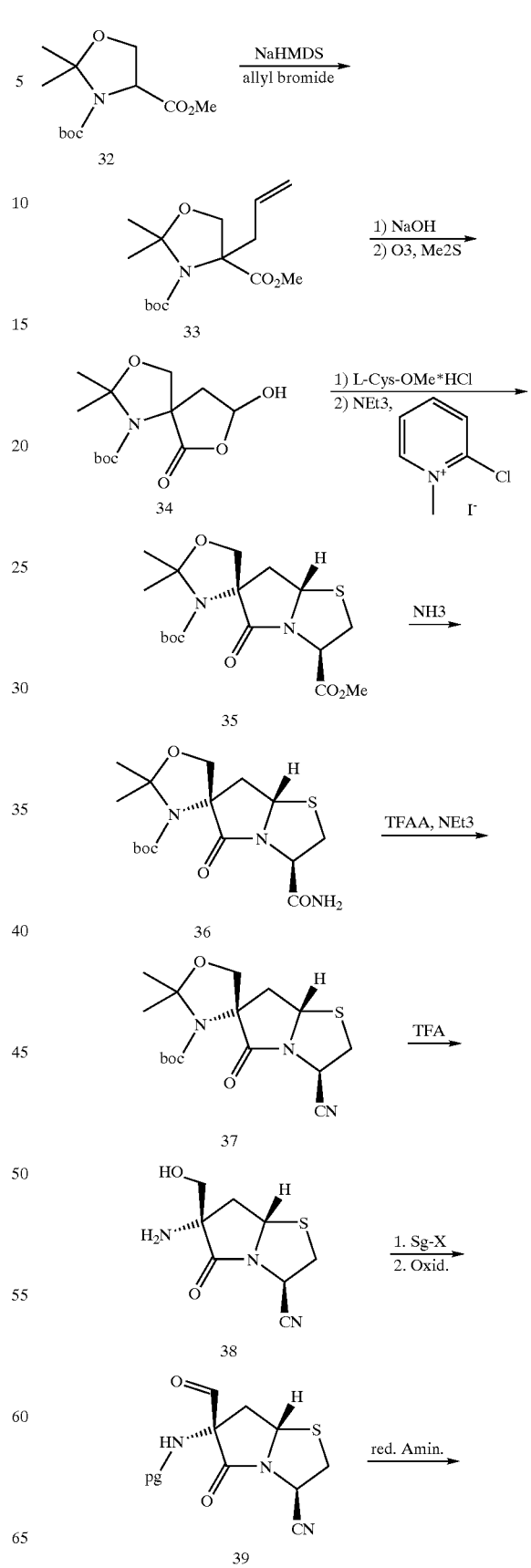

A further method for preparing the substances of the invention of the formula 1 begins starting from the commercially available ester 32. Deprotonation of 32 with suitable bases such as NaHMDS and alkylation with allyl bromide affords 33, which can be converted by hydrolysis for example with sodium hydroxide solution and by oxidation for example with ozone or osmium teroxide/sodium periodate into the cyclic aldehyde derivative 34. Condensation with L-cysteine methyl ester hydrochloride to give the thiazolidine and subsequent cyclization with acid activating agents such as, for example, 2-chloro-1-methylpyridinium iodide in the presence of triethylamine affords the tricyclic thiazolidide 35, which can be isolated in addition to other diastereomers of this constitution by usual separation processes such as column chromatography. The amide 36 is then obtained with ammonia in a known manner and is converted with trifluoroacetic anhydride in the presence of suitable bases such as triethylamine into the nitrile 37. Elimination of the protective groups with acidic reagents such as trifluoroacetic acid then affords the compound 38 which, after conversion into the protective aldehyde 39 (pg=protective group), can be converted by reductive amination (Nu=residue of a secondary amine) into 40 and further as mentioned above into the substances of the formula 41.

-continued

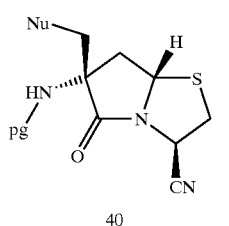
40

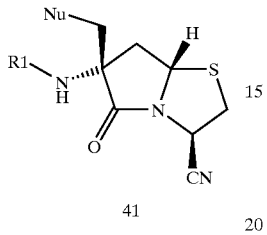
41

A further possibility for preparing compounds of the formula 41 consists of initially producing compound 42 as shown below by metallic reduction from 23 (R2=CH₂—OBn). Double protection of hydroxy group and carboxylic acid with tert-butyl-dimethylsilyl chloride (TBSCl) and imidazole, and subsequent hydrolysis of the silyl ester affords compound 43. The cyclic aldehyde derivative 44 is obtained by reaction with osmium tetroxide and sodium periodate. Condensation with cysteine derivatives (e.g. L-cysteine methyl ester hydrochloride) and subsequent cyclization with acid activating agents such as, for example, 1-(3-dimethylaminopropyl)-3-ethylcarbodiimide hydrochloride (EDC) results in the diastereomeric bicycles 45 and 46. These can be separated by usual methods, for example by chromatography. Elimination of the silyl group from 45 by usual methods (e.g. tetrabutylammonium fluoride in THF) affords 47. Oxidation of the alcohol function by known processes (e.g. Dess-Martin-periodinane) and reductive amination (Nu=residue of a primary or secondary amine) then produces the compounds 48. The amide is prepared therefrom with ammonia and is converted with acid activating reagents (e.g. trifluoroacetic anhydride in the presence of triethylamine) into the nitrile 49. Elimination of the Boc protective group with acidic reagents (e.g. trifluoroacetic acid) then affords the compounds 41.

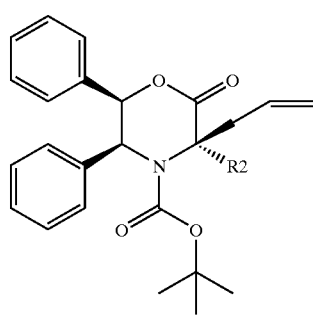
23
R2 = —CH2—O-Bn

-continued

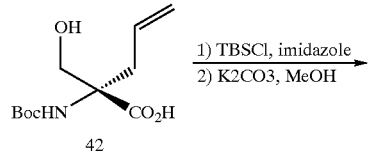
42

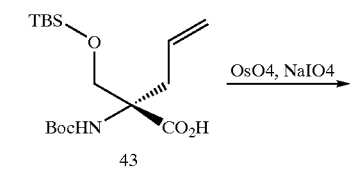
43

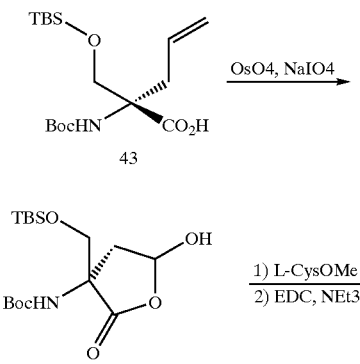
44

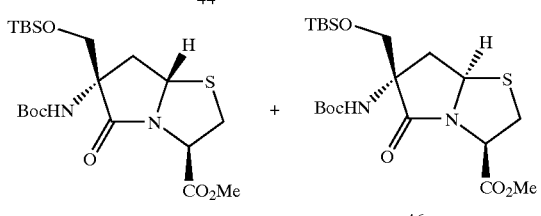
45    46

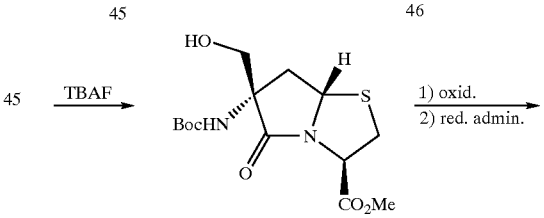
47

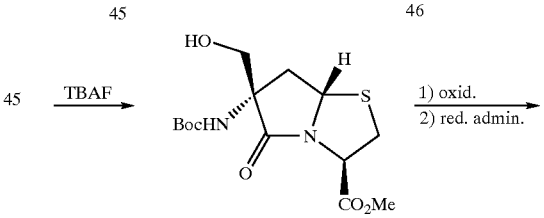
48

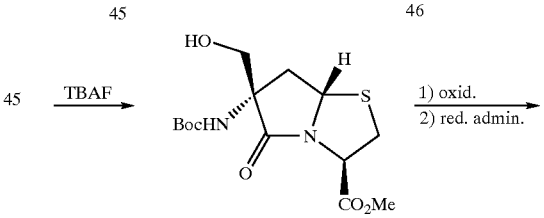
49

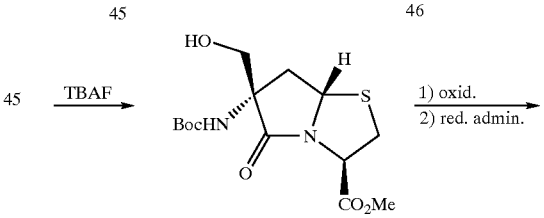
41

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of bodyweight, for example 3–10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compound(s) of formula (I) may also be administered in combination with other active ingredients.

Further active ingredients suitable for combination products are:

all antidiabetics mentioned in the Rote Liste 2003, chapter 12. They may be combined with the compounds of the formula I of the invention in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964, fast-acting insulins (see U.S. Pat. No. 6,221,633), GLP-1 derivatives such as, for example, those disclosed in WO 97/26265, WO 99/03861, WO 01/04156, WO 00/34331, WO 00/34332, WO 91/11457 and U.S. Pat. No. 6,380,357 and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside or compounds as described in WO 02/50027 or WO 04/007455.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 11833, PCT/US 11490, DE 10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor (see, for example, U.S. Pat. No. 6,245, 744 or U.S. Pat. No. 6,221,897), such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer (see U.S. Pat. No. 6,342,512), such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3, 4-dihydro-3-methyl-4-oxo-2-quinazolinylmethoxy]-phenyl] methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554–558), NPY antagonists, (e.g. naphthalene-1-sulfonic acid{4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid[2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-yl-urea hydrochloride (SB-334867-A)), cannabinoid 1 receptor antagonists (e.g. rimonabant or compounds as described in WO 02/28346), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2 -carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873–881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615–1622.

In one embodiment, the other active ingredient is dexamphetamine or amphetamine.

In one embodiment, the other active ingredient is a blood pressure reducing agent, such as, for example, an ACE inhibitor.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In one embodiment, the other active ingredient is rimonabant.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September–October), 18(5), 230–6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

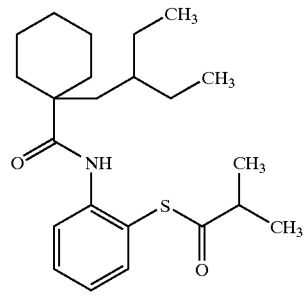

JTT-705

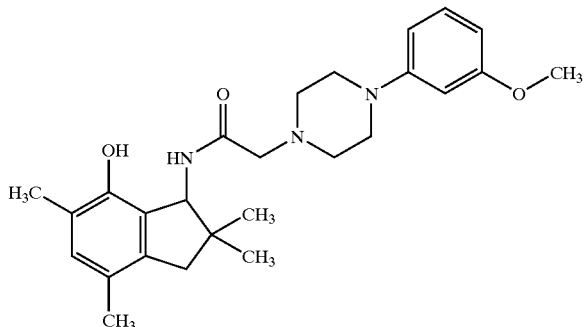

OPC-14117

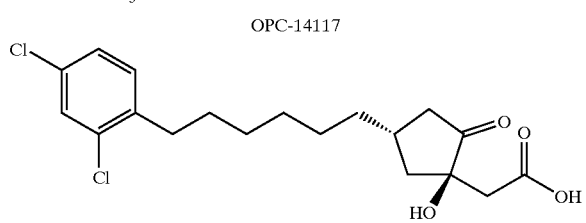

SB-204990

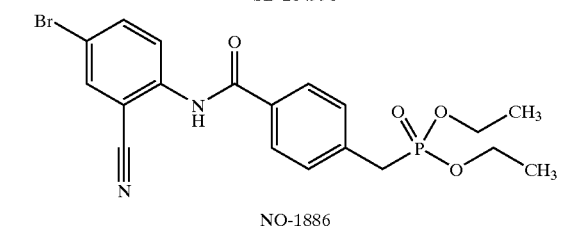

NO-1886

-continued

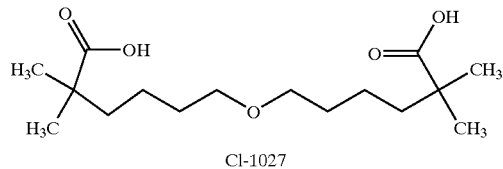
Cl-1027

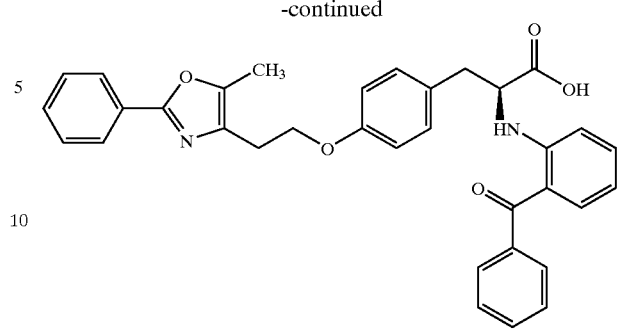
GI 262570

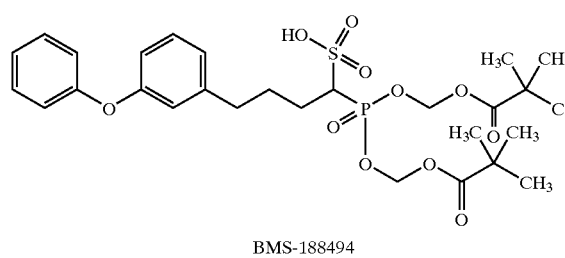
BMS-188494

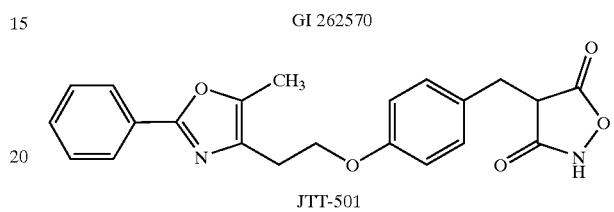
JTT-501

The theoretical examples listed in Table I below serve to illustrate the invention. They can be prepared in analogy to the exemplary embodiments.

TABLE I

Formula I

| | R1 | R2 | X |
|---|---|---|---|
| a | H | Me | S |
| b | H | i-Pr | S |
| c | H | Me | SO |
| d | H | Me | SO$_2$ |
| e | H | c-hexyl | S |
| f | Me | H | S |
| g | i-Pr | H | S |
| h | i-Pr | H | SO |
| I | i-Pr | Me | S |
| j | 1-adamantyl | H | S |
| k | 1-hydroxyadamant-3-yl | H | S |
| l | Ph | H | S |
| m | 2-pyridyl | H | S |
| n | —(CH2)2—NH-2-pyridyl | H | S |
| o | 1,1-dimethyl-2-phenyl | H | S |
| p | (4-methylcyclohexyl)-NH-C(O)-cyclohexyl | H | S |
| q | (4-methylpiperidin-1-yl)-C(O)-cyclohexyl | H | S |
| r | Me | —CH2—CH(CH3)2 | S |

TABLE I-continued

Formula I

|   | R1 | R2 | X |
|---|---|---|---|
| s | Et | ethyl-piperidine | S |
| t | —CH2—CH2—OH | —CH2—CH(CH3)2 | S |
| u | —CH2—CH2—OCH3 | ethyl-phenyl | S |
| v | —CH2—CH2—N(CH3)2 | —CH2—CH(CH3)2 | S |
| w | 2-pyridyl | Me | S |
| x | 2-thienyl | ethyl-phenyl | S |
| y | —CH2—CH(CH3)2 | —CH2—CH(CH3)2 | S |
| aa | c-pentyl | CH2—CH2—CH3 | S |
| ba | H | CH2—CH=C(CH3)2 | S |
| ca | H | CH3 | S |
| da | H | CH2—CH3 | S |
| ea | H | CH2OH | S |
| fa | H | CH2—O—CH3 | S |
| ga | H | CH2—O—CH2—CH3 | S |
| ha | H | CH2—S—CH3 | S |
| ia | H | CH2—CH2—N(CH2—CH3)2 | S |
| ja | H | CH2—C(CH3)3 | S |
| la | H | C(CH3)3 | S |
| ma | H | CH(CH3)(Ph) | S |
| na | H | CH2—S—Ph | S |
| oa | H | CH2—O—(C6H4-4-Cl) | S |
| pa | H | CH2—CH2—CH(CH3)2 | S |
| qa | H | CH2—N(CH3)2 | S |
| ra | H | CH2—N(CH2—CH3)2 | S |
| sa | H | ethyl-cyclohexyl | S |
| ta | H | ethyl-cyclopentyl | S |
| ua | H | ethyl-morpholine | S |
| va | H | ethyl-(4-methylcyclohexyl) | S |
| wa | H | ethyl-(4-hydroxymethylcyclohexyl) | S |

TABLE I-continued

Formula I

|  | R1 | R2 | X |
|---|---|---|---|
| xa | H | 4-ethylcyclohexyl-OH | S |
| ya | H | 4-ethylcyclohexyl-OMe | S |
| za | H | methylcyclohexyl | S |
| ab | H | methylcyclopentyl | S |
| bb | H | 4-ethylcyclohexyl-NH₂ | S |
| cb | H | 1-ethylpiperidin-4-yl-NH₂ | S |
| db | H | N-ethyl-cyclohexylamine | S |
| eb | H | 4-ethylcyclohexyl-N(CH₃)₂ | S |
| fb | H | 4-methylpiperidin-NH | SO |
| gb | H | 4-ethyl-1-methylpiperidine | S |
| hb | H | 1-ethylpiperazine-NH | S |
| ib | H | 1-ethyl-4-methylpiperazine | S |

TABLE I-continued
Formula I
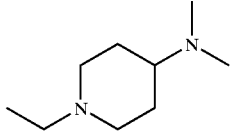
| | R1 | R2 | X |
|---|---|---|---|
| jb | H | 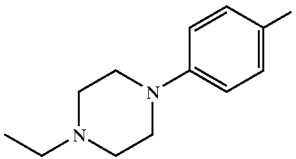 | S |
| kb | H | 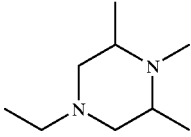 | S |
| lb | H | 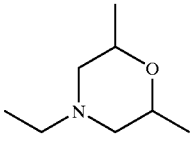 | S |
| mb | H | 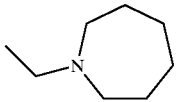 | S |
| nb | H | 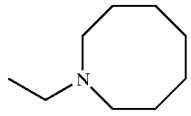 | S |
| ob | H | 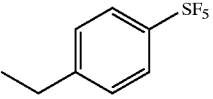 | S |
| pb | H | 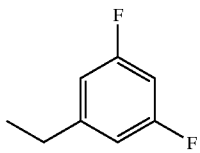 | S |
| qb | H | 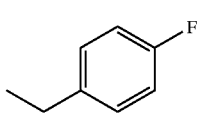 | S |
| rb | H | | S |

TABLE I-continued
Formula I
| | R1 | R2 | X |
|---|---|---|---|
| sb | H | 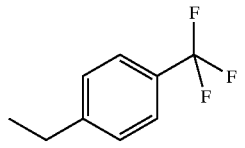 | S |
| tb | H | 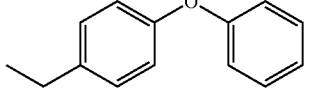 | S |
| ub | H | 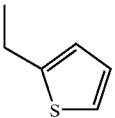 | S |
| vb | H | 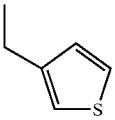 | S |
| wb | H | 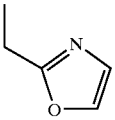 | S |
| xb | H | 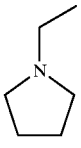 | S |
| yb | H | 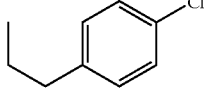 | S |
| zb | H | 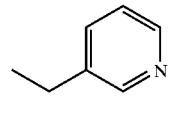 | S |
| ac | H | 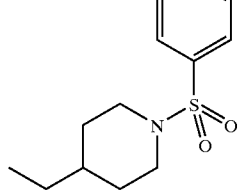 | S |

TABLE I-continued

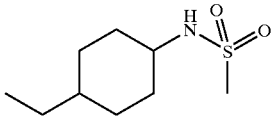
Formula I

| | R1 | R2 | X |
|---|---|---|---|
| bc | H | 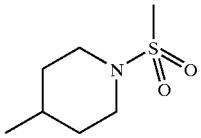 | S |
| cc | H | 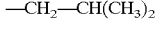 | S |
| cd | H | —CH$_2$—CH(CH$_3$)$_2$ | SO |
| ce | H | 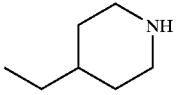 | SO |
| cf | H | 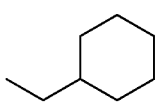 | SO |
| cg | H | —CH$_2$—CH(CH$_3$)$_2$ | SO2 |
| | | eI | |

The compounds of the formula I are notable for beneficial effects on lipid and carbohydrate metabolism, in particular they lower the blood glucose level and are suitable for the treatment of type 2 diabetes, of insulin resistance, of dyslipidemias and of metabolic syndrome/syndrome X. The compounds are also suitable for the prophylaxis and treatment of arteriosclerotic manifestations. The compounds can be employed alone or in combination with other blood glucose-lowering active ingredients. The compounds act as DPP-IV inhibitors and are also suitable for the treatment of disorders of wellbeing and other psychiatric indications such as, for example, depressions, anxiety states, anxiety neuroses, schizophrenia and for the treatment of disorders associated with the circadian rhythm, for weight reduction in mammals, for the treatment of immunological disorders, and for the treatment of drug abuse. They are also suitable for the treatment of cancer, arthritis, osteoarthritis, osteoporosis, sleep disorders, sleep apnea, female and male sexual disorders, inflammations, acne, pigmentation of the skin, disorders of steroid metabolism, skin diseases, psoriasis, mycoses, neurodegenerative diseases, multiple sclerosis and Alzheimer's disease.

The activity of the compounds was assayed as follows:

Activity Assay

Measurement of the DPP-IV activity:

Material:

DPP-IV from porcine kidney (Sigma, Munich)
H-Ala-Pro-AFC (Bachem, Weil am Rhein)

Assay Conditions:

DPP-IV (1 mU/ml, final concentration)

H-Ala-Pro-AFC (15 μM, final concentration) in Tris/HCl (40 mM, pH 7.4), total volume 0.2 ml The reaction was carried out at room temperature for various times (typically 10 min) and stopped at the end of the reaction by adding 20 μl of ZnCl$_2$(1M). The H-Ala-Pro-AFC conversion was determined fluorimetrically by measuring the emission at 535 nm after excitation at 405 nm. When inhibitors were added, the added buffer volume was adapted so that a total volume of 200 μl was maintained for the assay mixture.

IC50 values for inhibitors were determined by varying the inhibitor concentrations with the stated substrate concentration of 15 μM. Ki and Km values were found by appropriate variation of substrate concentration and inhibitor concentration as described (Dixon, M. and Webb, E. C. (1979) Enzymes, third edition, pp. 47–206, Academic Press). The values for Km, IC50 and Ki were calculated using a commercially available software package (Leatherbarrow, R. J. (1992) GraFit Version 3.0, Erithacus Software Ltd. Staines, U.K.).

The measurements yielded the following values:

| Exemplary embodiment No. | IC-50 | Remarks |
|---|---|---|
| 1) | 48 nM | Trifluoroacetic acid salt |
| 2) | 47 nM | Trifluoroacetic acid salt |
| 6) | 2 μM | Trifluoroacetic acid salt |

-continued

| Exemplary embodiment No. | IC-50 | Remarks |
| --- | --- | --- |
| 7) | 18 nM | Trifluoroacetic acid salt |
| 8) | 400 nM | Trifluoroacetic acid salt |
| 9) | 110 nM | Trifluoroacetic acid salt |
| 10) | 300 nM | Bistrifluoroacetic acid salt |
| 11) | 500 nM | Bistrifluoroacetic acid salt |

Exemplary embodiments 1 to 11 were prepared as follows:

1) (3R,6R,7aS)-6-Amino-6-benzyl-5-oxohexahydropyrrolo[2,1-b]thiazole-3-carbonitrile trifluoroacetate

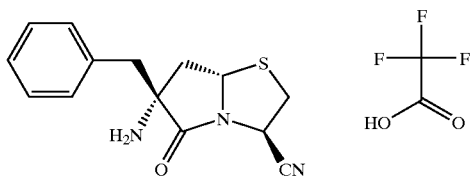

1a) Allyl (2S,4S)-4-benzyl-2-tert-butyl-5-oxooxazolidine-3-carboxylate

A mixture consisting of 5 g of (S)-phenylalanine and 30.5 ml of 1 molar sodium hydroxide solution is stirred at RT for 1 h and then evaporated to dryness in vacuo at 60° C. Addition of 50 ml of toluene is followed by renewed evaporation to dryness at 40° C., and the residue is suspended in 100 ml of n-pentane, mixed with 7.7 ml of trimethylacetaldehyde and stirred under reflux in an oil bath with a water trap for 15 h. The volatile constituents were removed in vacuo at 40° C., and the residue is mixed with 40 ml of toluene each time and evaporated to dryness in vacuo. The residue is then suspended in 100 ml of methylene chloride and stirred in an ice bath, and 3.53 ml of allyl chloroformate are added. The mixture was stirred without renewing the ice bath while gradually reaching room temperature for 4 days. The product mixture was partitioned between 100 ml of methylene chloride and 75 ml of saturated brine, the insoluble solid was removed by filtration with suction, and the organic phase was washed 3 times with saturated sodium bicarbonate solution (30 ml each time) and then once more with saturated brine, dried over sodium sulfate and concentrated in vacuo. The oily residue was purified by column chromatography (silica gel, mobile phase: heptane.ethyl acetate=45:5).

Yield: 3.4 g; m.p.: oil; M+H: 274

1b) Allyl (2S,4S)-4-allyl-4-benzyl-2-tert-butyl-5-oxooxazolidine-3-carboxylate 3.16 g of allyl (2S,4S)-4-benzyl-2-tert-butyl-5-oxooxazolidine-3-carboxylate in 20 ml of tetrahydrofuran are cooled in a dry ice bath to −65° C. under argon, and 20.9 ml of a 0.5 molar solution of potassium bistrimethylsilylamide in toluene are added dropwise, and the mixture is stirred at this temperature for 30 minutes. Then 0.861 ml of allyl bromide are added dropwise, and the mixture is stirred while gradually warming to room temperature. After being left to stand overnight, 15 ml of saturated ammonium chloride solution were added, and the product was extracted with ethyl acetate. Washing of the ethyl acetate solution with saturated brine was followed by evaporation in vacuo and purification of the product by column chromatography (silica gel, mobile phase: ethyl acetate:heptane=5:45).

Yield: 2.0 g; m.p.: oil; M+H: 358

1c) (S)-2-Amino-2-benzylpent-4-enecarboxylic acid

A mixture of 2 g of allyl (2S,4S)-4-allyl-4-benzyl-2-tert-butyl-5-oxooxazolidine-3-carboxylate, 60 ml of tetrahydrofuran, 4.88 ml of morpholine and 300 mg of tetrakistriphenylphosphinepalladium is stirred at room temperature for 20 minutes and then concentrated in vacuo. The residue is stirred in a mixture of 6 ml of glacial acetic acid and 20 ml of water for 30 minutes. After the volatile constituents have been stripped off in vacuo at 40° C., the product is purified by column chromatography (silica gel, mobile phase: methylene chloride:methanol=9:1).

Yield: 680 mg m.p.: 221.2° C. M+H: 206

1d) (S)-2-Benzyl-2-tert-butoxycarbonylaminopent-4-enecarboxylic acid 2.2 ml of 1N sodium hydroxide solution are added to a solution of 450 mg of (S)-2-amino-2-benzylpent-4-enecarboxylic acid in 8 ml of dioxane and 6 ml of water, and then 1.6 g of di-tert-butyl dicarbonate and 350 mg of potassium carbonate are added to the mixture, which is stirred at 40° C. for 7 hours. The dioxane is then stripped off in vacuo at room temperature, and the aqueous phase is adjusted to pH=3–4 with 10% strength citric acid and extracted with ethyl acetate (10 ml). The organic phase is dried over sodium sulfate and concentrated, and the oily residue is used unpurified for the further reactions.

Yield: 490 mg m.p.: oil M+H: 306

1e) Methyl (S)-2-benzyl-2-tert-butoxycarbonylaminopent-4-enecarboxylate

A total of 5 ml of a 2 molar solution of trimethylsilyldiazomethane in hexane is added in portions to a solution of 490 mg of (S)-2-benzyl-2-tert-butoxycarbonylaminopent-4-enecarboxylic acid in 8 ml of methanol while stirring at room temperature. After the reaction is complete, the excess trimethylsilyldiazomethane is destroyed by dropwise addition of glacial acetic acid, and the volatile constituents are stripped off in a rotary evaporator at 40° C. The residue is purified on a column (silica gel, mobile phase: methylene chloride:methanol=95:5).

Yield: 410 mg m.p.: oil M+H: 320

1f) Methyl (R)-2-benzyl-2-tert-butoxycarbonylamino-4-oxobutyrate 1.1 ml of a 2.5% strength solution of osmium tetroxide in tert-butanol and then, in portions, 686 mg of sodium periodate are added to a solution of 410 mg of methyl (S)-2-benzyl-2-tert-butoxycarbonylaminopent-4-enecarboxylate in 15 ml of tetrahydrofuran and 5 ml of water under nitrogen, and the mixture is stirred at room temperature overnight. The volatile constituents are removed in vacuo, and the residue is taken up in 26 ml of 1N sodium bicarbonate solution, and the product is extracted with diethyl ether. Drying and concentration result in an oil.

Yield: 400 mg m.p.: oil M+H: 322

1 g) (3R,6R,7aS)-6-Benzyl-6-tert-butoxycarbonylamino-5-oxohexahydropyrrolo[2,1-b]thiazole-3-carboxylic acid A mixture consisting of 400 mg of methyl (R)-2-benzyl-2-tert-butoxycarbonylamino-4-oxobutyrate, 5 ml of pyridine and 166 mg of L-cysteine is heated under reflux for 4 hours. After concentration in vacuo at 50° C., the product is purified by column chromatography (silica gel, mobile phase: methylene chloride:methanol:glacial acetic acid=90:10:1).

Yield: 375 mg m.p.: oil M+H: 393

1h) Methyl (3R,6R,7aS)-6-benzyl-6-tert-butoxycarbonylamino-5-oxohexahydropyrrolo[2,1-b]thiazole-3-carboxylate A total of 1.5 ml of a 2 molar solution of trimethylsilyldiazomethane in hexane is added in portions to a solution of 250 mg of (3R,6R,7aS)-6-benzyl-6-tert-butoxycarbonylamino-5-oxohexahydropyrrolo[2,1-b]thiazole-3-carboxylic acid in 8 ml of methanol while stirring at room temperature. After the reaction is complete, the excess trimethylsilyldiazomethane is destroyed by dropwise addition of glacial acetic acid, and the volatile constituents are stripped off in a rotary evaporator at 40° C. The residue is purified on a column (silica gel, mobile phase:ethyl acetate:n-heptane=1:1.5).

Yield: 250 mg m.p. oil M+H: 407

1i) (3R,6R,7aS)-6-Benzyl-6-tert-butoxycarbonylamino-5-oxohexahydropyrrolo[2,1-b]thiazole-3-carboxamide A mixture of 170 mg of methyl (3R,6R,7aS)-6-benzyl-6-tert-butoxycarbonylamino-5-oxohexahydropyrrolo[2,1-b]thiazole-3-carboxylate and 10 ml of a 7N NH3 solution in methanol is left to stand at room temperature overnight. The volatile constituents are stripped off in vacuo, and the residue is stirred with tert-butyl methyl ether, and the solid is filtered off with suction and dried in vacuo at 40° C.

Yield: 130 mg m.p.: 76.5° C. M+H: 392

1j) tert-Butyl (3R,6R,7aS)-(6-benzyl-3-cyano-5-oxohexahydropyrrolo[2,1-b]thiazol-6-yl)-carbamate 100 mg of (3R,6R,7aS)-6-benzyl-6-tert-butoxycarbonylamino-5-oxohexahydropyrrolo[2,1-b]thiazole-3-carboxamide are dissolved in 3 ml of dimethylformamide and reacted with 28.25 mg of cyanuric chloride at room temperature. After 2 hours, the volatile constituents are stripped off in vacuo at 40° C., and the residue is purified on a column (silica gel, mobile phase: diisopropyl ether:methylene chloride=100:10).

Yield: 50 mg m.p.: oil M+H: 374

1k) (3R,6R,7aS)-6-Amino-6-benzyl-5-oxohexahydropyrrolo[2,1-b]thiazole-3-carbonitrile trifluoroacetate A mixture consisting of 50 mg of tert-butyl (3R,6R,7aS)-(6-benzyl-3-cyano-5-oxohexahydropyrrolo[2,1-b]thiazol-6-yl)-carbamate, 0.1 ml of thioanisole and 1 ml of trifluoroacetic acid is stirred in an ice bath for 15 minutes. After room temperature was reached, the mixture was concentrated in vacuo at 40° C., and the residue was stirred with diisopropyl ether and the solid product was filtered off with suction.

Yield: 35 mg m.p.: 209° C. M+H: 274

2) (3R,6R,7aS)-6-Amino-5-oxohexahydropyrrolo[2,1-b]thiazole-3-carbonitrile trifluoroacetate

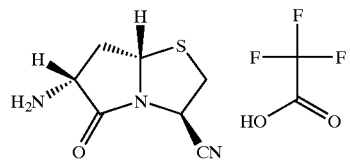

2a) tert-Butyl (R)-(5-hydroxy-2-oxotetrahydrofuran-3-yl)-carbamate

A total of 13.4 g of sodium periodate is added in portions to a mixture consisting of 5.3 g of (R)—N—BOC-allylglycine, 80 ml of tetrahydrofuran, 300 ml of water and 16 ml of a 2.5% strength solution of osmium tetroxide in tert-butanol. After stirring at room temperature overnight, the precipitate is filtered off with suction, and the filtrate is concentrated in vacuo. The residue is taken up in 500 ml of 1N sodium bicarbonate solution and extracted with 2 portions of 250 ml of diethyl ether. The aqueous phase was adjusted to pH=2 with 2N hydrochloric acid and again extracted with ether. The combined organic phases were dried over sodium sulfate and evaporated to dryness in vacuo at room temperature. The residue was stirred with n-heptane, the solid portion of product was filtered off with suction, and the filtrate was concentrated, resulting in a somewhat impure oily product.

| Yield: 1.58 g | m.p: 112.4° C. | M + H: 218 |
| Yield: 1.2 g | m.p.: oil | M + H: 218 |

2b) Methyl (2RS,4R)-2-((R)-2-tert-butoxycarbonylamino-2-carboxyethyl)-thiazolidine-4-carboxylate A mixture of 2.7 g of tert-butyl (R)-(5-hydroxy-2-oxotetrahydrofuran-3-yl)-carbamate, 46 ml of ethanol and 46 ml of water is adjusted to pH=5 with sodium bicarbonate and, after addition of 2.2 g of L-cysteine methyl ester hydrochloride, stirred at room temperature for 3 hours. The volatile solvents were stripped off in vacuo at 40° C., the aqueous phase has a pH of about 7 and is extracted with ethyl acetate, and this organic phase is discarded. The remaining aqueous solution is adjusted to pH=5 by adding glacial acetic acid and the product is extracted with 2 portions each of 20 ml of ethyl acetate. The organic phase is dried over sodium sulfate and concentrated in vacuo.

Yield: 1.2 g m.p.: resin M+H: 335

A further 2.4 g of impure product can be obtained from the aqueous phase by concentration and stirring with methylene chloride.

2c) Methyl (3R,6R,7aS)-6-tert-butoxycarbonylamino-5-oxohexahydropyrrolo[2,1-b]thiazole-3-carboxylate and 2d) Methyl (3R, 6R, 7aR)-6-tert-butoxycarbonylamino-5-oxohexahydropyrrolo[2,1-b]thiazole-3-carboxylate A mixture consisting of 3.6 g of methyl (2RS, 4R)-2-((2R)-2-tert-butoxycarbonylamino-2-carboxyethyl)-thiazolidine-4-carboxylate, 62 ml of methylene chloride, 3.3 g of 2-chloromethylpyridinium iodide and 3.6 ml of triethylamine is left to stand at room temperature for 2 days. This mixture is washed with 50 l of 1N citric acid solution and then 30 ml of 1N sodium bicarbonate solution, dried over sodium sulfate and concentrated in vacuo. Two products are obtained from the oily residue by column chromatography (silica gel, mobile phase: ethyl acetate:n-heptane=1:1). (3R, 6R,7aS) isomer, nonpolar compound 2c:

Yield: 1080 mg m.p.: resin M+H: 317

(3R,6R,7aR) isomer, polar compound 2d:

Yield: 820 mg m.p.: resin M+H: 317

2e) tert-Butyl (3R,6R,7aS)-(3-carbamoyl-5-oxohexahydropyrrolo[2,1-b]thiazol-6-yl)-carbamate 850 mg of methyl (3R,6R,8S)-6-tert-butoxycarbonylamino-5-oxohexahydropyrrolo[2,1-b]thiazole-3-carboxylate (2c) were dissolved in 30 ml of 7 N NH3 solution in methanol and left to stand at room temperature overnight. After concentration in vacuo at 40° C., the product was purified by stirring in tert-butyl methyl ether and filtration with suction, and dried in vacuo.

Yield: 250 mg m.p.: 189.4° C. M+H: 302

2f) tert-Butyl (3R,6R,7aR)-(3-carbamoyl-5-oxohexahydropyrrolo[2,1-b]thiazol-6-yl)-carbamate was obtained in analogy to the synthesis of 2e) starting from 540 mg of methyl (3R,6R,8R)-6-tert-butoxycarbonylamino-5-oxohexahydropyrrolo[2,1-b]thiazole-3-carboxylate (2d).

Yield: 250 mg m.p.: resin M+H: 317

2g) tert-Butyl (3R,6R,7aS)-(3-cyano-5-oxohexahydropyrrolo[2,1-b]thiazol-6-yl)-carbamate A solution of 538 mg of tert-butyl (3R,6R,7aS)-(3-carbamoyl-5-oxohexahydropyrrolo[2,1-b]thiazol-6-yl)-carbamate in 35 ml of tetrahydrofuran was cooled in an ice bath and, after addition of 0.75 ml of triethylamine and 0.37 ml of trifluoroacetic anhydride, stirred at room temperature overnight. The volatile constituents were stripped off in vacuo at 30° C., and the oily residue was purified by column chromatography (silica gel, mobile phase: ethyl acetate:n-heptane=1:1).

Yield: 320 mg m.p.: 191.2° C. M+H: 284

2h) tert-Butyl (3R, 6R, 7aR)-(3-cyano-5-oxohexahydropyrrolo[2,1-b]thiazol-6-yl)-carbamate was obtained in analogy to the synthesis of 2g), starting from 238 mg of tert-butyl (3R,6R,7aR)-(3-carbamoyl-5-oxohexahydropyrrolo[2,1-b]thiazol-6-yl)-carbamate.

Yield: 130 mg m.p.: oil M+H: 284

2i) (3R,6R,7aS)-(6-Amino-5-oxohexahydropyrrolo[2,1-b]thiazole-3-carbonitrile trifluoroacetate A solution of 300 mg of tert-butyl (3R,6R,7aS)-(3-cyano-5-oxohexahydropyrrolo[2,1-b]thiazol-6-yl)-carbamate in 10 ml of methylene chloride is cooled in an ice bath, 1.5 ml of trifluoroacetic acid are added, and the mixture is stirred while gradually reaching room temperature for 2 hours. The volatile constituents were removed in vacuo at 40° C., and the residue was stirred with diisopropyl ether and the solid was filtered off with suction.

Yield: 280 mg m.p.: 180.3° C. M+H: 184

3) (3R, 6R, 7aR)-(6-Amino-5-oxohexahydropyrrolo[2,1-b]thiazole-3-carbonitrile trifluoroacetate

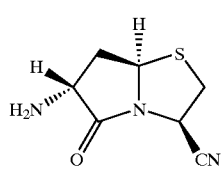 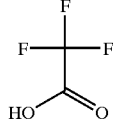

was obtained in analogy to the synthesis of 2i) starting from 130 mg of tert-butyl (3R, 6R, 7aR)-(3-cyano-5-oxohexahydropyrrolo[2,1-b]thiazol-6-yl)-carbamate.

Yield: 105 mg m.p.: 173.5° C. M+H: 184

4) (3R,6R,7aS)-5-Oxo-6-(3-phenylpropylamino)-hexahydropyrrolo[2,1-b]thiazole-3-carbonitrile

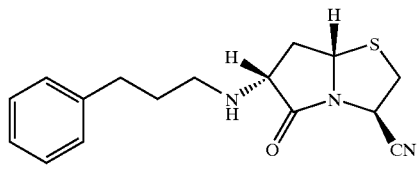

30 mg of (3R,6R,7aS)-(6-amino-5-oxohexahydropyrrolo[2,1-b]thiazole-3-carbonitrile trifluoroacetate, 0.0132 ml of 3-phenylpropionaldehyde and 0.115 ml of glacial acetic acid were heated in 1.5 ml of methylene chloride at 40° C. for 20 minutes. The mixture was then cooled to room temperature, 8.3 mg of sodium acetate, 0.5 ml of dimethoxyethane and 27.8 mg of sodium triacetoxyborohydride were added, and the mixture was stirred at RT overnight. After concentration of the mixture, the residue was purified by column chromatography (silica gel, mobile phase: ethyl acetate: n-heptane=8:1).

Yield: 13 mg m.p.: oil M+H: 302

5) (3R,6R,7aS)-6-Benzylamino-5-oxohexahydropyrrolo[2,1-b]thiazole-3-carbonitrile trifluoroacetate 20 mg of (3R,6R,7aS)-6-amino-5-oxohexahydropyrrolo[2,1-b]thiazole-3-carbonitrile trifluoroacetate were dissolved in 1 ml of 1,2-dichloroethane. 2 μl of acetic acid, 7 μl of benzaldehyde and 29 mg of sodium triacetoxyborohydride were successively added. The mixture was heated at 45° C. for 2 h. The solvent was then removed in vacuo. The residue was purified by preparative HPLC (Merck RP18, acetonitrile/water (0.5% trifluoroacetic acid), linear gradient (0–>80% acetonitrile)).

Yield: 5 mg of (3R,6R,(S)-6-benzylamino-5-oxohexahydropyrrolo[2,1-b]thiazole-3-carbonitrile trifluoroacetate

MS: 274 (M+H)

6) (3R,6R,7aS)-6-Cyclopentylamino-5-oxohexahydropyrrolo[2,1-b]thiazole-3-carbonitrile trifluoroacetate 20 mg of (3R,6R,7aS)-6-amino-5-oxohexahydropyrrolo[2,1-b]thiazole-3-carbonitrile trifluoroacetate were dissolved in 1 ml of 1,2-dichloroethane. 2 μl of acetic acid, 6 μl of cyclopentanone and 29 mg of sodium triacetoxyborohydride were successively added. The mixture was heated at 45° C. for 2 h. The solvent was then removed in vacuo. The residue was purified by preparative HPLC (Merck RP18, acetonitrile/water (0.5% trifluoroacetic acid), linear gradient (0–>80% acetonitrile)).

Yield: 15 mg of 6-cyclopentylamino-5-oxohexahydropyrrolo[2,1-b]thiazole-3-carbonitrile trifluoroacetate

MS: 252 (M+H)

7) (3R,6R,7aS)-6-Amino-6-isobutyl-5-oxohexahydropyrrolo[2,1-b]thiazole-3-carbonitrile trifluoroacetate

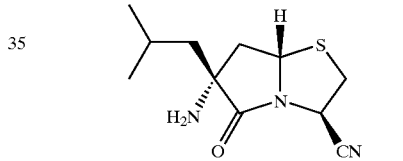 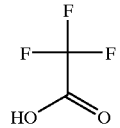

7a) tert-Butyl (3S,5S,6R)-3-allyl-2-oxo-5,6-diphenylmorpholine-4-carboxylate 10 g of tert-butyl (5S,6R)-2-oxo-5,6-diphenylmorpholine-4-carboxylate were dissolved in 200 ml of THF and cooled to −78° C. 63 ml of a 0.5 M solution of KHMDS in toluene were added dropwise and, after stirring for 10 min, 3.7 ml of allyl bromide were added dropwise. The mixture was allowed to warm from −78° C. to −20° C. over the course of 3 h, and the reaction was then stopped by adding 300 ml of a saturated ammonium chloride solution. 200 ml of ethyl acetate were added, and the phases were separated. The aqueous phase was extracted 3 times with 100 ml of ethyl acetate each time, and the combined organic phases were dried with MgSO4. The solvents were removed in vacuo and the residue was stirred with diisopropyl ether.

Yield: 7.3 g of tert-butyl (3S,5S,6R)-3-allyl-2-oxo-5,6-diphenylmorpholine-4-carboxylate MS: 338 (M+H-tBu)

7b) tert-Butyl (3R,5S,6R)-3-allyl-3-isobutyl-2-oxo-5,6-diphenylmorpholine-4-carboxylate 1 g of tert-butyl (3S,5S,6R)-3-allyl-2-oxo-5,6-diphenylmorpholine-4-carboxylate was dissolved in 20 ml of THF. 3 ml of 15-crown-5 were added, and the mixture was cooled to −78° C. Then 1.4 ml of a 2 M solution of NaHMDS in THF were added dropwise. The mixture was stirred for 10 min and then 300 μl of isobutyl iodide were added dropwise.

The temperature was allowed to rise to 0° C. over the course of 6 h, and then the reaction was stopped by adding 50 ml of saturated ammonium chloride solution. The aqueous phase was extracted 3 times with 50 ml of ethyl acetate each time, and the combined organic phases were dried with MgSO4. The solvents were removed in vacuo and the residue was chromatographed on silica gel with heptane/ethyl acetate 10:1.

Yield: 620 mg of tert-butyl (3R,5S,6R)-3-allyl-3-isobutyl-2-oxo-5,6-diphenyl-morpholine-4-carboxylate MS: 394 (M+H-tBu)

7c) (R)-2-tert-Butoxycarbonylamino-2-isobutylpent-4-enoic acid 60 ml of ammonia were condensed at −78° C. Then 624 mg of sodium were added in 2 portions at an interval of 10 min. The mixture was stirred for 20 min. At −60° C., a solution of tert-butyl (3R,5S,6R)-3-allyl-3-isobutyl-2-oxo-5,6-diphenylmorpholine-4-carboxylate 1.22 g and 1.6 ml of ethanol in 20 ml of THF was added dropwise thereto. The mixture was stirred at −45° C. for 1.5 h, and the reaction was stopped by adding solid ammonium chloride until the blue color disappeared. The ammonia is then allowed to evaporate off, and 50 ml of water are added to the residue. The THF is removed in vacuo. The aqueous is adjusted to pH 2 with 1 N HCl and extracted 3 times with 60 ml of ethyl acetate each time. The combined organic phases are dried with MgSO4. The solvents are removed in vacuo and the residue is purified by chromatography on silica gel.

Yield: 508 mg of (R)-2-tert-butoxycarbonylamino-2-isobutylpent-4-enoic acid

MS: 172 (M+H-Boc)

7d) Methyl (3R,6R,7aS)-6-tert-butoxycarbonylamino-6-isobutyl-5-oxohexahydropyrrolo[2,1-b]thiazole-3-carboxylate and 7e) Methyl (3R,6R,7aR)-6-tert-butoxycarbonylamino-6-isobutyl-5-oxohexahydropyrrolo[2,1-b]thiazole-3-carboxylate 500 mg of (R)-2-tert-butoxycarbonylamino-2-isobutylpent-4-enoic acid were dissolved in 20 ml of THF and 5 ml of water. A solution of 24 mg of osmium tetroxide in 2 ml of THF was added dropwise thereto and, after stirring for 5 min, 985 mg of sodium periodate were added. The mixture was stirred for 3 h and then filtered through kieselguhr. The filter cake was washed twice with 10 ml of THF each time. The THF was removed in vacuo, and the residue was partitioned between 60 ml of ethyl acetate and 30 ml of water. The pH was adjusted to 2 with 1 N HCl solution. The phases were separated and the aqueous phase was extracted twice with 20 ml of ethyl acetate each time. The combined organic phases were dried with MgSO4 and the solvents were removed in vacuo. The residue was chromatographed on silica gel with 5% methanol in dichloromethane. This resulted in 410 mg of the cyclic aldehyde derivative which were dissolved in 10 ml of dichloromethane. While stirring, 230 μl of triethylamine and 258 mg of L-cysteine methyl ester hydrochloride were added. The mixture was stirred at room temperature for 2.5 h and then 317 mg of 1-(3-dimethylaminopropyl)-3-ethylcarbodiimide hydrochloride were added. After stirring at room temperature for 14 hours, the reaction was diluted with 80 ml of dichloromethane and washed twice with 80 ml of water each time. The organic phase was dried with MgSO4 and the solvents were removed in vacuo. The diastereomeric compounds methyl (3R,6R,7aS)-6-tert-butoxycarbonylamino-6-isobutyl-5-oxohexahydropyrrolo[2,1-b]thiazole-3-carboxylate and methyl 3R,6R,7R-6-tert-butoxycarbonylamino-6-isobutyl-5-oxo-hexahydropyrrolo[2,1-b]thiazole-3-carboxylate were separated by chromatography on silica gel.

Yield: 75 mg of 7d) methyl (3R,6R,7aS)-6-tert-butoxycarbonylamino-6-isobutyl-5-oxohexahydropyrrolo[2,1-b]thiazole-3-carboxylate MS: 373 (M+H) and 304 mg of 7e) methyl (3R,6R,7aR)-6-tert-butoxycarbonylamino-6-isobutyl-5-oxohexahydropyrrolo[2,1-b]thiazole-3-carboxylate

MS: 373 (M+H)

7f) (3R,6R,7aS)-6-tert-Butoxycarbonylamino-6-isobutyl-5-oxohexahydropyrrolo[2,1-b]thiazole-3-carboxamide 71 mg of methyl (3R,6R,7aS)-6-tert-butoxycarbonylamino-6-isobutyl-5-oxohexahydropyrrolo[2,1-b]thiazole-3-carboxylate were dissolved in 10 ml of ammonia-saturated methanol and cooled to 0° C. The mixture was allowed slowly to reach room temperature and was stirred for 14 h. The solvents were removed in vacuo. The crude product was employed without further purification in the next reaction.

MS: 302 (M+H-tBu)

7g) tert-Butyl (3R,6R,7aS)-(3-cyano-6-isobutyl-5-oxohexahydropyrrolo[2,1-b]thiazole-6-yl)-carbamate The crude product from 2e was dissolved in 5 ml of THF. 63 μl of triethylamine and 29 μl of trifluoroacetic anhydride were added thereto. The mixture was stirred at room temperature for 3 h and then partitioned between 60 ml of water and 60 ml of ethyl acetate. The aqueous phase was extracted twice with 50 ml of ethyl acetate each time, and the combined organic phases were dried with MgSO4. The solvents were removed in vacuo and the residue was purified by chromatography on silica gel.

Yield: 57 mg of tert-butyl (3R,6R,7aS)-(3-cyano-6-isobutyl-5-oxohexahydropyrrolo[2,1-b]thiazol-6-yl)-carbamate MS: 284 (M+H-tBu)

7h) (3R,6R,7aS)-6-Amino-6-isobutyl-5-oxohexahydropyrrolo[2,1-b]thiazole-3-carbonitrile trifluoroacetate 53 mg of tert-butyl (3R,6R,7aS)-(3-cyano-6-isobutyl-5-oxohexahydropyrrolo[2,1-b]thiazol-6-yl)-carbamate were reacted with 3 ml of trifluoroacetic acid and 600 μl of thioanisole at 0° C. for 30 min. The solvents were then removed in vacuo, and the residue was stirred in diethyl ether, filtered off with suction and dried.

Yield: 39 mg of (3R,6R,7aS)-6-amino-6-isobutyl-5-oxohexahydropyrrolo[2,1-b]thiazole-3-carbonitrile trifluoroacetate

MS: 240 (M+H)

7i) (3R,6R,7aR)-6-Amino-6-isobutyl-5-oxohexahydropyrrolo[2,1-b]thiazole-3-carbonitrile trifluoroacetate

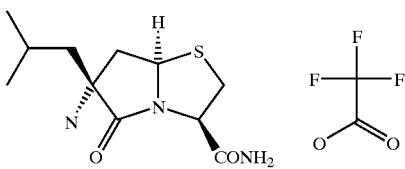

was obtained in analogy to Examples 7f), 7g) and 7h) starting from the diastereomer 7e).

MS: 240 (M+H)

8) (3R,6S,7aS)-6-Amino-6-hydroxymethyl-5-oxohexahydropyrrolo[2,1-b]thiazole-3-carbonitrile trifluoroacetate

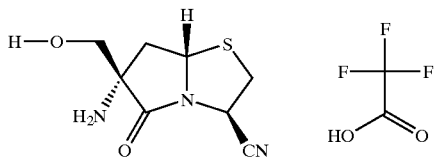

8a) 3-tert-Butyl 4-methyl 4-allyl-2,2-dimethyloxazolidine-3,4-dicarboxylate 10 g of 3-tert-butyl 4-methyl 2,2-dimethyloxazolidine-3,4-dicarboxylate were dissolved in 270 ml of THF. After cooling to −78° C., 100 ml of a 0.5 M solution of KHMDS in toluene were added dropwise. After stirring at −78° C. for 30 min, 5.4 ml of allyl bromide were added dropwise. The mixture was allowed slowly to reach room temperature and was stirred for 14 h. The reaction was then stopped by adding 400 ml of saturated ammonium chloride solution. The THF was removed in vacuo and the aqueous phase was extracted 3 times with 150 ml of ethyl acetate each time. The combined organic phases were washed once with 300 ml of saturated sodium chloride solution and dried with MgSO4. The solvents were removed in vacuo and the residue was chromatographed on silica gel.

Yield: 5.58 g of 3-tert-butyl 4-methyl 4-allyl-2,2-dimethyloxazolidine-3,4-dicarboxylate MS: 322 (M+Na)

8b) tert-Butyl 8-hydroxy-2,2-dimethyl-6-oxo-3,7-dioxa-1-azaspiro[4.4]nonane-1-carboxylate

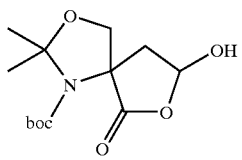

1.7 g of 3-tert-butyl 4-methyl 4-allyl-2,2-dimethyloxazolidine-3,4-dicarboxylate were dissolved in 20 ml of methanol and 8 ml of 1 N NaOH were added. The mixture was heated at 60° C. for 3 h, allowed to cool, and the methanol was removed in vacuo. The pH of the aqueous phase was adjusted to 2 with 1 N HCl, and it was extracted 3 times with 50 ml of dichloromethane each time. The combined organic phases were dried with MgSO4, and the solvent was removed in vacuo. The residue was taken up in 80 ml of dichloromethane and 10 ml of methanol. The solution was cooled to −78° C., and ozone was passed through until it assumed a pale blue color. Argon was then passed through until the blue color had completely disappeared. 3 ml of dimethyl sulfide were added, and the mixture was allowed to reach room temperature overnight. The solvents were then removed in vacuo. The crude product obtained in this way was employed directly in the next reaction.

8c) Acetonide of (3R,6S,7aS)-6-(tert-butyloxycarbonylamino)-6-hydroxymethyl-5-oxohexahydropyrrolo[2,1-b]thiazole-3-carboxamide

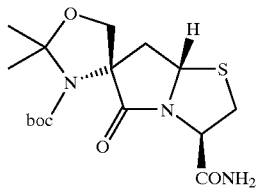

The crude product from 8b was dissolved in 40 ml of ethanol. The solution was cooled to 0° C. and, under argon, 500 mg of sodium bicarbonate in 5 ml of water, and 1 g of L-cysteine methyl ester hydrochloride were added. The pH of the solution was adjusted to 6.5 with 1% sodium bicarbonate solution in water. The mixture was allowed slowly to reach room temperature and was stirred for 14 h. The volume was then reduced to about one half in vacuo. The pH was adjusted to 6 with 1 N HCl, and the aqueous phase was extracted with 70 ml of ethyl acetate. This procedure was repeated three times. The combined organic phases were dried with MgSO4. The solvents were then removed in vacuo. The residue was taken up in 400 ml of 1,2-dichloroethane, and 1.7 g of 2-chloro-1-methylpyridinium iodide and 1.9 ml of triethylamine were added. The mixture was heated at 50° C. for 4 h. It is then washed once with 150 ml of 1 N HCl and 150 ml of saturated sodium bicarbonate solution. The organic phase is dried with MgSO4. The solvents are removed in vacuo, and the residue is taken up in 60 ml of ammonia-saturated methanol. The mixture was stirred for 18 h, the solvents were removed in vacuo, and the residue was chromatographed on silica gel.

Yield: 230 mg of the compound of the above formula

MS: 316 (M+H-tBu)

8d) Acetonide of (3R,6S,7aS)-6-(tert-butyloxycarbonylamino)-6-hydroxymethyl-5-oxohexahydropyrrolo[2,1-b]thiazole-3-carbonitrile

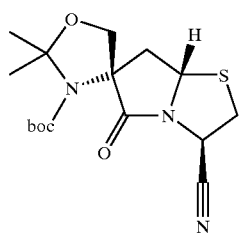

200 mg of the compound 8c were dissolved in 5 ml of THF. 188 μl of triethylamine and 114 μl of trifluoroacetic anhydride were successively added. The mixture was then stirred at room temperature for 6 h. The solution was partitioned between 60 ml of saturated sodium bicarbonate solution and 60 ml of ethyl acetate. The aqueous phase was extracted twice with 30 ml of ethyl acetate each time, and the combined organic phases were dried with MgSO4. The solvents were removed in vacuo and the residue was purified by chromatography on silica gel.

Yield: 90 mg of the acetonide of the above formula

MS: 240

49

8e) (3R,6S,7aS)-6-Amino-6-hydroxymethyl-5-oxo-hexahydropyrrolo[2,1-b]thiazole-3-carbonitrile trifluoroacetate 5 mg of the compound 8d were dissolved in 2 ml of dichloromethane and cooled to 0° C. 300 µl of TFA were added, and the mixture was stirred at 0° C. for 4 h. The solvents were then removed in vacuo, and the residue was stirred with diethyl ether.

Yield: 5 mg

MS: 214 (M+H)

9) (3R,6S,7aS)-6-Amino-5-oxo-6-piperidin-1-ylmethyl)-hexahydropyrrolo[2,1-b]thiazole-3-carbonitrile bistrifluoroacetate

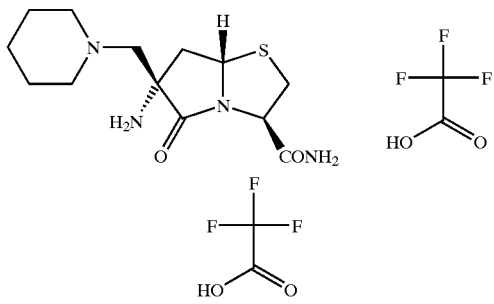

9a) tert-Butyl (3S,5S,6R)-3-allyl-3-benzyloxymethyl-2-oxo-5,6-diphenylmorpholine-4-carboxylate 5.7 g of tert-butyl 3S,5S,6R-3-allyl-2-oxo-5,6-diphenylmorpholine-4-carboxylate were dissolved in 150 ml of THF. 8.6 ml of 15-crown-5 were added and the mixture was cooled to −78° C. Then 8 ml of a 2 M solution of NaHMDS in THF were added dropwise. The mixture was stirred for 10 min and then 6.7 ml of benzyloxymethyl chloride were added dropwise. The mixture was allowed to warm to 0° C. over the course of 6 h, and then the reaction was stopped by adding 200 ml of saturated ammonium chloride solution. The aqueous phase was extracted 3 times with 150 ml of ethyl acetate each time, and the combined organic phases were dried with MgSO4. The solvents were removed in vacuo, and the residue was chromatographed on silica gel with heptane/ethyl acetate 10:1.

Yield: 620 mg of tert-butyl (3S,5S,6R)-3-allyl-3-benzyloxymethyl-2-oxo-5,6-diphenyl-morpholine-4-carboxylate MS: 458 (M+H-tBu)

9b) (S)-2-tert-Butoxycarbonylamino-2-hydroxymethyl-pent-4-enoic acid 450 ml of ammonia were condensed at −78° C. 4.4 g of sodium were added in 4 portions at an interval of 10 min each time, and the mixture was stirred for 20 min. At −60° C., a solution of 9.8 g of tert-butyl (3S,5S,6R)-3-allyl-3-benzyloxymethyl-2-oxo-5,6-diphenylmorpholine-4-carboxylate and 11.2 ml of ethanol in 150 ml of THF was added dropwise thereto. The mixture was stirred at −45° C. for 1.5 h, and the reaction was stopped by adding solid ammonium chloride until the blue color disappeared. The ammonia was then allowed to evaporate off, and 400 ml of water were added to the residue. The THF was removed in vacuo. The aqueous was adjusted to pH 2 with 1 N HCl and extracted 3 times with 200 ml of ethyl acetate each time. The combined organic phases were dried with MgSO4. The solvents

50 were removed in vacuo and the residue was purified by chromatography on silica gel.

Yield: 2.6 g of (S)-2-tert-butoxycarbonylamino-2-hydroxymethylpent-4-enoic acid

MS: 146 (M+H-Boc)

9c) (S)-2-tert-Butoxycarbonylamino-2-(tert-butyldimethylsilanyloxymethyl)-pent-4-enoic acid 1.3 g of (S)-2-tert-butoxycarbonylamino-2-hydroxymethylpent-4-enoic acid were dissolved in 10 ml of dimethylformamide. 1.44 g of imidazole and 1.7 g of tert-butyldimethylsilyl chloride were added thereto. The mixture was stirred at room temperature for 14 h and then partitioned between 150 ml of water and 200 ml of diethyl ether. The aqueous phase was extracted twice with 100 ml of diethyl ether each time, and the combined organic phases were dried with MgSO4. The solvents were removed in vacuo and the residue was taken up in 20 ml of THF and 60 ml of methanol. 11 ml of a 1 M potassium carbonate solution were added, and the mixture was stirred at room temperature for 2 h. Then 150 ml of a saturated sodium chloride solution were added, and the pH of the solution was adjusted to 2 with 1 M HCL solution. The aqueous phase was extracted 3 times with 100 ml of ethyl acetate each time, and the combined organic phases were dried with MgSO4. The solvents were removed in vacuo, and the crude product was employed without further purification in the next reaction.

Yield: 1.8 g of (S)-2-tert-butoxycarbonylamino-2-(tert-butyldimethylsilanyloxymethyl)-pent-4-enoic acid MS: 260 (M+H-Boc)

9d) Methyl (3R,6S,7aS)-6-tert-butoxycarbonylamino-6-(tert-butyldimethylsilanyloxymethyl)-5-oxohexahydropyrrolo[2,1-b]thiazole-3-carboxylate and 9e) Methyl (3R,6S,7aR)-6-tert-butoxycarbonylamino-6-(tert-butyldimethylsilanyloxymethyl)-5-oxohexahydropyrrolo[2,1-b]thiazole-3-carboxylate 3.7 g of (S)-2-tert-butoxycarbonylamino-2-(tert-butyldimethylsilanyloxymethyl)-pent-4-enoic acid were dissolved in 1220 ml of THF and 30 ml of water. 131 mg of osmium tetroxide were added, and the mixture was stirred for 5 min. Then 5.5 g of sodium periodate were added. The mixture was stirred at room temperature for 2 h and then filtered through kieselguhr. The filter cake was washed twice with 30 ml of THF each time. The THF was then removed in vacuo, and the residue was partitioned between 150 ml of diethyl ether and 100 ml of saturated sodium bicarbonate solution. The aqueous phase was adjusted to pH 1 with 1 N HCl and extracted 3 times with 100 ml of ethyl acetate each time. The combined organic phases were dried with MgSO4. The solvents were removed in vacuo, and the residue was taken up in 40 ml of ethanol. The mixture was cooled to −20° C. and, under argon, 864 mg of sodium bicarbonate dissolved in 40 ml of water were added. Then 1.77 g of L-cysteine methyl ester hydrochloride were added, and the pH of the solution was adjusted to 6.5 with 1% strength sodium bicarbonate solution. The mixture was stirred at room temperature for 14 h. The solution was then concentrated in vacuo to half the volume. The pH was adjusted to 6 with 1 N HCl, and the solution was extracted with 100 ml of ethyl acetate. Adjustment of the pH to 6 and extraction with ethyl acetate was repeated 3 times. The combined organic phases were dried with MgSO4. The solvents were removed in vacuo, and the residue was taken up in 200 ml of THF. 3.2 ml of triethylamine and 2.9 g of 1-(3-dimethylaminopropyl)-3-ethylcarbodiimide hydrochloride were added. The mixture was then stirred at room temperature for 1 h and at 50° C. for 3 h. The solvent was removed in vacuo, and the residue was partitioned between 100 ml of 1 N HCl and 100 ml of ethyl acetate. The aqueous phase was extracted twice with 50 ml of ethyl acetate each time, and the combined organic phases were dried with MgSO4. The solvents were removed in vacuo, and the residue was purified by chromatography on silica gel.

Yield: 340 mg of 9d) methyl (3R,6S,7aS)-6-tert-butoxycarbonylamino-6-(tert-butyldimethylsilanyloxymethyl)-5-oxohexahydropyrrolo[2,1-b]thiazole-3-carboxylate MS: 405 (M+H-tBu) and 1.1 g of 9e) methyl (3R,6S,7aR)-6-tert-butoxycarbonylamino-6-(tert-butyldimethylsilanyloxymethyl)-5-oxohexahydropyrrolo[2,1-b]thiazole-3-carboxylate MS: 405 (M+H-tBu)

9f) Methyl (3R,6S,7aS)-6-tert-butoxycarbonylamino-6-hydroxymethyl-5-oxohexahydropyrrolo[2,1-b]thiazole-3-carboxylate 337 mg of methyl (3R,6S,7aS)-6-tert-butoxycarbonylamino-6-(tert-butyldimethylsilanyloxymethyl)-5-oxohexahydropyrrolo[2,1-b]thiazole-3-carboxylate were dissolved in 10 ml of THF and cooled to 0° C. A 1 M solution of tetrabutylammonium fluoride was added dropwise, and the mixture was allowed to reach room temperature within 2 h. It was then partitioned between 120 ml of saturated ammonium chloride solution and 120 ml of ethyl acetate. The aqueous phase was extracted twice with 40 ml of ethyl acetate each time. The combined organic phases were washed once with 80 ml of saturated sodium chloride solution and dried with MgSO4. The solvents were removed in vacuo, and the residue was purified by chromatography on silica gel.

Yield: 180 mg of methyl (3R,6S,7aS)-6-tert-butoxycarbonylamino-6-hydroxymethyl-5-oxohexahydropyrrolo[2,1-b]thiazole-3-carboxylate MS: 291 (M+H-tBu)

9g) Methyl (3R,6S,7aS)-6-tert-butoxycarbonylamino-5-oxo-6-piperidin-1-ylmethyl)-hexahydropyrrolo[2,1-b]thiazole-3-carboxylate 170 mg of methyl (3R,6S,7aS)-6-tert-butoxycarbonylamino-6-hydroxymethyl-5-oxohexahydropyrrolo[2,1-b]thiazole-3-carboxylate were dissolved in 5 ml of dichloromethane. 400 µl of pyridine and 230 mg of Dess-Martin-periodinane were added. The mixture was then stirred at room temperature for 2 h. The solution was partitioned between 20 ml of 0.5 M HCl and 20 ml of dichloromethane. The aqueous phase was extracted twice with 10 ml of dichloromethane each time, and the combined organic phases were dried with MgSO4. The solvent was removed in vacuo, and the residue was taken up in 5 ml of 1,2-dichloroethane. 49 µl of piperidine, 15 µl of acetic acid and 209 mg of sodium triacetoxyborohydride were successively added. The mixture was then stirred at room temperature for 14 h. The solution was partitioned between 30 ml of saturated sodium bicarbonate solution and 20 ml of dichloromethane. The aqueous phase was extracted twice with 10 ml of dichloromethane each time, and the combined organic phases were dried with MgSO4. The solvents were removed in vacuo and the residue was chromatographed on silica gel.

Yield: 30 mg of methyl (3R,6S,7aS)-6-tert-butoxycarbonylamino-5-oxo-6-piperidin-1-ylmethyl)-hexahydropyrrolo[2,1-b]thiazole-3-carboxylate

MS: 414 (M+H)

9h) (3R,6S,7aS)-6-Amino-5-oxo-6-(piperidin-1-ylmethyl)-hexahydropyrrolo[2,1-b]thiazole-3-carbonitrile bistrifluoroacetate 30 mg of methyl (3R,6S,7aS)-6-tert-butoxycarbonylamino-5-oxo-6-(piperidin-1-yl-methyl)-hexahydropyrrolo[2,1-b]thiazole-3-carboxylate were dissolved at 0° C. in 30 ml of ammonia-saturated methanol. The solution was allowed to reach room temperature over the course of 4 h, and then the solvents were removed in vacuo. The residue was taken up in 5 ml of THF, and 40 µl of triethylamine and 20 µl of trifluoroacetic anhydride were successively added. The mixture was stirred at room temperature for 2 h and then a further 40 µl of triethylamine and 20 µl of trifluoroacetic anhydride were added. Stirring for 2 h was followed by partition between 60 ml of 0.5 M HCl and 60 ml of ethyl acetate. The aqueous phase was extracted twice with 20 ml of ethyl acetate each time, and the combined organic phases were washed once with 30 ml of saturated sodium bicarbonate solution. After drying with MgSO4, the solvents were removed in vacuo. The residue was taken up in a mixture of 1 ml of trifluoroacetic acid and 200 µl of thioanisole and stirred at room temperature for 20 min. The trifluoroacetic acid was then removed in vacuo, and the residue was chromatographed on silica gel with dichloromethane/methanol/acetic acid/water 100:10:1:1.

Yield: 31 mg of (3R,6S,7aS)-6-amino-5-oxo-6-(piperidin-1-ylmethyl)-hexahydropyrrolo[2,1-b]thiazole-3-carbonitrile bistrifluoroacetate.

MS: 281 (M+H)

9i) (3R,6S,7aR)-6-Amino-5-oxo-6-(piperidin-1-ylmethyl)-hexahydropyrrolo[2,1-b]thiazole-3-carbonitrile bistrifluoroacetate

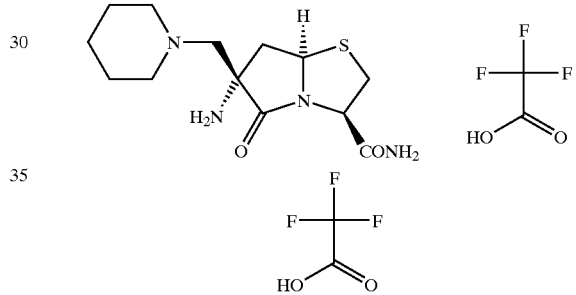

was prepared analogously to Examples 9f), 9g) and 9h) starting from the diastereomer 9e).

MS: 281 (M+H)

10) (3R,6S,7aS)-6-Amino-5-oxo-6-(piperidin-4-yl)-hexahydropyrrolo[2,1-b]thiazole-3-carbonitrile bistrifluoroacetate

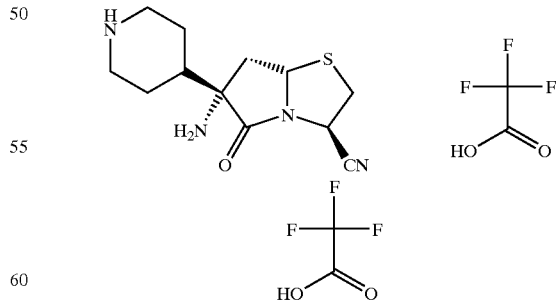

10a) 2-Trimethylsilanylethyl 4-hydroxypiperidine-1-carboxylate 6.9 g of 4-hydroxypiperidine were dissolved in 150 ml of THF. 19.4 g of 2-(trimethylsilyl)ethyl 4-nitrophenyl carbonate and 11.9 ml of N,N-diisopropylethylamine were successively added thereto. The mixture was stirred at room temperature for 1 h and then the solvent was removed in vacuo. The residue was taken up in 400 ml of ethyl acetate and washed once with 200 ml of 0.5 N HCl and twice with 200 ml of 1 N NaOH each time. The organic phase was dried with MgSO4, the solvent was removed in vacuo, and the residue was purified by chromatography on silica gel.

Yield: 15.4 g of 2-trimethylsilanylethyl 4-hydroxypiperidine-1-carboxylate

MS: 218 (M+H-C2H4)

10b) 2-Trimethylsilanylethyl 4-iodopiperidine-1-carboxylate 12.5 g of 2-trimethylsilanylethyl 4-hydroxypiperidine-1-carboxylate were dissolved in 136 ml of dichloromethane and 264 ml of tetrachloromethane. The solution was cooled to 0° C. and then 16 g of triphenylphosphine, 4.2 g of imidazole and 15.8 g of iodine were successively added. The mixture was slowly allowed to reach room temperature and was stirred for 14 h. Then 300 ml of a saturated sodium thiosulfate solution were added to the solution. The mixture was stirred until it was colorless. The aqueous phase was then extracted twice with 200 ml of dichloromethane each time. The combined organic phases were washed once with 200 ml of a saturated sodium thiosulfate solution and once with 200 ml of a saturated sodium chloride solution. After drying with MgSO4, the solvents were removed in vacuo, and the residue was purified by chromatography on silica gel.

Yield: 8 g of 2-trimethylsilanylethyl 4-iodopiperidine-1-carboxylate

MS: 328 (M+H-C2H4)

10c) tert-Butyl (3R,5R,6S)-2-oxo-5,6-diphenyl-3-[1-(2-trimethylsilanylethoxycarbonyl)-piperidin-4-yl]morpholine-4-carboxylate 4 g of tert-butyl (5S,6R)-2-oxo-5,6-diphenylmorpholine-4-carboxylate were dissolved in 50 ml of THF. 9 ml of 15-crown-5 were added, and the mixture was cooled to −78° C. Then 6.8 ml of a 2 M solution of NaHMDS in THF were added dropwise. The mixture was stirred for 10 min and then 8 g of 2-trimethylsilanylethyl 4-iodopiperidine-1-carboxylate were added dropwise. The mixture was allowed to warm to 0° C. over the course of 6 h, and then the reaction was stopped by adding 200 ml of saturated ammonium chloride solution. The aqueous phase was extracted 3 times with 150 ml of ethyl acetate each time, and the combined organic phases were dried with MgSO4. The solvents were removed in vacuo, and the residue was chromatographed on silica gel.

Yield: 1.82 g of tert-butyl (3R,5R,6S)-2-oxo-5,6-diphenyl-3-[1-(2-trimethylsilanylethoxycarbonyl)piperidin-4-yl]morpholine-4-carboxylate MS: 497 (M+H-C2H4-tBu)

10d) tert-Butyl (3S,5R,6S)-3-allyl-2-oxo-5,6-diphenyl-3-[1-(2-trimethylsilanylethoxycarbonyl)piperidin-4-yl]morpholine-4-carboxylate 1.8 g of tert-butyl (3R,5R,6S)-2-oxo-5,6-diphenyl-3-[1-(2-trimethylsilanylethoxycarbonyl)piperidin-4-yl]morpholine-4-carboxylate were dissolved in 20 ml of THF. 2.5 ml of 15-crown-5 were added, and the mixture was cooled to −78° C. Then 1.9 ml of a 2 M solution of NaHMDS in THF were added dropwise. The mixture was stirred for 10 min and then 805 µl of allyl bromide were added dropwise. The mixture was allowed to warm to 0° C. over the course of 6 h, and then the reaction was stopped by adding 100 ml of saturated ammonium chloride solution. The aqueous phase was extracted 3 times with 100 ml of ethyl acetate each time, and the combined organic phases were dried with MgSO4. The solvents were removed in vacuo, and the residue was chromatographed on silica gel.

Yield: 916 mg of tert-butyl (3S,5R,6S)-3-allyl-2-oxo-5,6-diphenyl-3-[1-(2-trimethylsilanylethoxycarbonyl)piperidin-4-yl]morpholine-4-carboxylate

MS: 593 (M+H-C2H4)

10e) 2-Trimethylsilanylethyl 4-((S)-1-tert-butoxycarbonylamino-1-methoxycarbonyl-but-3-enyl)piperidine-1-carboxylate 50 ml of ammonia were condensed at −78° C. 340 mg of sodium were added in 2 portions at an interval of 10 min in each case and the mixture was stirred for 20 min. At −60° C., a solution of 916 mg of tert-butyl (3S,5R,6S)-3-allyl-2-oxo-5,6-diphenyl-3-[1-(2-trimethylsilanylethoxycarbonyl)piperidin-4-yl]morpholine-4-carboxylate and 866 µl of ethanol in 50 ml of THF was added dropwise. The mixture was stirred at −45° C. for 1.5 h, and the reaction was stopped by adding solid ammonium chloride until the blue color disappeared. The ammonia was then allowed to evaporate off, and 150 ml of water were added to the residue. The THF was removed in vacuo. The aqueous was adjusted to pH 2 with 1 N HCl and extracted 3 times with 100 ml of ethyl acetate each time. The combined organic phases were dried with MgSO4. The solvents were removed in vacuo, and the residue was filtered through silica gel with 4% methanol in dichloromethane. The product obtained in this way was taken up in 5 ml of methanol and cooled to 0° C. 0.5 ml of a 2 N solution of trimethylsilyldiazomethane in hexane was added thereto 5 times at intervals of 1.5 hours each. 2 ml of acetic acid were then added dropwise, and the mixture was stirred at room temperature for 1 h. The solvents were removed in vacuo and the residue was chromatographed on silica gel.

Yield: 233 mg of 2-trimethylsilanylethyl 4-((S)-1-tert-butoxycarbonylamino-1-methoxycarbonylbut-3-enyl)piperidine-1-carboxylate MS: 373 (M+H-C2H4-tBu)

10f) (3R,6S,7aS)-6-tert-Butoxycarbonylamino-5-oxo-6-[1-(2-trimethylsilanylethoxycarbonyl)piperidin-4-yl]hexahydropyrrolo[2,1-b]thiazole-3-carboxylic acid 230 mg of 2-trimethylsilanylethyl 4-((S)-1-tert-butoxycarbonylamino-1-methoxycarbonylbut-3-enyl)piperidine-1-carboxylate were dissolved in 25 ml of THF and 5 ml of water. Under argon, 157 µl of a 4% strength solution of osmium tetroxide in water and 269 mg of sodium periodate were added. The mixture was stirred at room temperature for 2 h and then filtered through kieselguhr. The filter cake was washed twice with 10 ml of THF each time. The THF was removed in vacuo, and the residue was partitioned between 20 ml of ethyl acetate and 10 ml of a saturated sodium chloride solution. The aqueous phase was extracted twice with 10 ml of ethyl acetate each time, and the combined organic phases were dried with MgSO4. The solvents were removed in vacuo, and the residue was taken up in 15 ml of pyridine. 61 mg of L-cysteine were added, and the mixture was heated at 100° C. for 24 h. The pyridine was then removed in vacuo, and the residue was chromatographed on silica gel.

Yield: 230 mg of (3R,6S,7aS)-6-tert-butoxycarbonylamino-5-oxo-6-[1-(2-trimethylsilanylethoxycarbonyl)piperidin-4-yl]hexahydropyrrolo[2,1-b]thiazole-3-carboxylic acid MS: 446 (M+H-C2H4-tBu)

10g) Methyl (3R,6S,7aS)-6-tert-butoxycarbonylamino-5-oxo-6-[1-(2-trimethylsilanylethoxycarbonyl)piperidin-4-yl]hexahydropyrrolo[2,1-b]thiazole-3-carboxylate 223 mg of (3R,6S,7aS)-6-tert-butoxycarbonylamino-5-oxo-6-[1-(2-trimethylsilanylethoxycarbonyl)piperidin-4-yl]hexahydropyrrolo[2,1-b]thiazole-3-carboxylic acid were dissolved in 10 ml of methanol and 10 ml of diethyl ether and cooled to 0° C. 400 µl portions of a 1 N solution of trimethylsilyldiazomethane in hexane were added dropwise twice at an interval of 1.5 h. The mixture was stirred for 2 h and then 1 ml of acetic acid was added dropwise. After 1 h, the solvents were removed in vacuo and the residue was purified by chromatogrpahy on silica gel.

Yield: 153 mg of methyl (3R,6S,7aS)-6-tert-butoxycarbonylamino-5-oxo-6-[1-(2-trimethylsilanylethoxycarbonyl)piperidin-4-yl]hexahydropyrrolo[2,1-b]thiazole-3-carboxylate MS: 460 (M+H-C2H4-tBu)

10h) 2-Trimethylsilanylethyl 4-((3R,6S,7aS)-6-tert-butoxycarbonylamino-3-cyano-5-oxohexahydropyrrolo[2,1-b]thiazol-6-yl)piperidine-1-carboxylate 153 mg of methyl (3R,6S,7aS)-6-tert-butoxycarbonylamino-5-oxo-6-[1-(2-trimethylsilanylethoxycarbonyl)piperidin-4-yl]hexahydropyrrolo[2,1-b]thiazole-3-carboxylate were dissolved at 0° C. in 30 ml of ammonia-saturated methanol. The mixture was allowed to reach room temperature over the course of 5 h, and then the solvents were removed in vacuo. The residue was taken up in 5 ml of THF, and 100 µl of triethylamine and 60 µl of trifluoroacetic anhydride were successively added. The mixture was stirred at room temperature for 2 h. It was then partitioned between 60 ml of 0.5 M HCl and 60 ml of ethyl acetate. The aqueous phase was extracted twice with 20 ml of ethyl acetate each time, and the combined organic phases were washed once with 30 ml of saturated sodium bicarbonate solution. After drying with MgSO4, the solvents were removed in vacuo. The residue was chromatographed on silica gel.

Yield: 108 mg of 2-trimethylsilanylethyl 4-((3R,6S,7aS)-6-tert-butoxycarbonylamino-3-cyano-5-oxohexahydropyrrolo[2,1-b]thiazol-6-yl)piperidine-1-carboxylate MS: 427 (M+H-C2H4-tBu)

10i) (3R,6S,7aS)-6-Amino-5-oxo-6-piperidin-4-ylhexahydropyrrolo[2,1-b]thiazole-3-carbonitrile bistrifluoroacetate 12 mg of 2-trimethylsilanylethyl 4-((3R,6S,7aS)-6-tert-butoxycarbonylamino-3-cyano-5-oxohexahydropyrrolo[2,1-b]thiazol-6-yl)piperidine-1-carboxylate were stirred in a mixture of 1 ml of trifluoroacetic acid and 200 µl of thioanisole at 0° C. for 40 min. The trifluoroacetic acid was removed in vacuo, and the residue was partitioned between 6 ml of water and 10 ml of ethyl acetate. The aqueous phase was washed 3 times with 5 ml of ethyl acetate each time. The water was then removed in vacuo, and the residue was stirred with diethyl ether.

Yield: 7 mg of (3R,6S,7aS)-6-amino-5-oxo-6-piperidin-4-ylhexahydropyrrolo[2,1-b]thiazole-3-carbonitrile bistrifluoroacetate

MS: 267 (M+H)

11) (3R,6R,7aS)-6-Amino-5-oxo-6-(piperidin-4-ylmethyl)hexahydropyrrolo[2,1-b]thiazole-3-carbonitrile bistrifluoroacetate

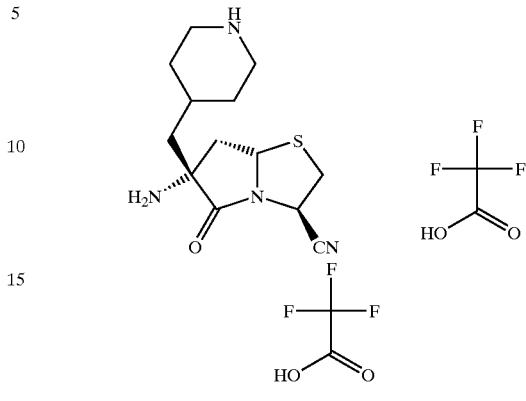

11a) 2-Trimethylsilanylethyl 4-hydroxymethylpiperidine-1-carboxylate 10.5 g of 4-piperidinylmethanol were dissolved in 170 ml of THF. 25.8 g of 2-(trimethylsilyl)ethyl 4-nitrophenyl carbonate and 15.9 ml of N,N-diisopropylethylamine were successively added thereto. The mixture was stirred at room temperature for 1 h and then the solvent was removed in vacuo. The residue was taken up in 400 ml of ethyl acetate and washed once with 300 ml of 0.5 N HCl and twice with 250 ml of 1 N NaOH each time. The organic phase was dried with MgSO4, the solvent was removed in vacuo, and the residue was purified by chromatography on silica gel.

Yield: 19.9 g of 2-trimethylsilanylethyl 4-hydroxymethylpiperidine-1-carboxylate

MS: 232 (M+H-C2H4)

11b) 2-Trimethylsilanylethyl 4-bromomethylpiperidine-1-carboxylate 19.9 g of 2-trimethylsilanylethyl 4-hydroxymethylpiperidine-1-carboxylate were dissolved in 600 ml of THF. After cooling to 0° C., 50.7 g of tetrabromomethane were added. Then 42.1 g of triphenylphosphine were added in 4 portions at intervals each of 20 min. The mixture was allowed to reach room temperature and was stirred for 14 h. The solvent was then removed in vacuo, and the residue was chromatographed on silica gel.

Yield: 22.2 g of 2-trimethylsilanylethyl 4-bromomethylpiperidine-1-carboxylate

MS: 294 (M+H-C2H4)

11c) tert-Butyl (3S,5S,6R)-3-allyl-2-oxo-5,6-diphenyl-3-[1-(2-trimethylsilanylethoxycarbonyl)piperidin-4-ylmethyl]morpholine-4-carboxylate 4.9 g of tert-butyl (3S,5S,6R)-3-allyl-2-oxo-5,6-diphenyl-morpholine-4-carboxylate were dissolved in 100 ml of THF. 14.9 ml of 15-crown-5 were added, and the mixture was cooled to −78° C. Then 6.8 ml of a 2 M solution of NaHMDS in THF were added dropwise. The mixture was stirred for 10 min and then 8 g of 2-trimethylsilanylethyl 4-bromomethylpiperidine-1-carboxylate were added dropwise. The mixture was allowed to warm to 0° C. over the course of 6 h, and the reaction was then stopped by adding 500 ml of saturated ammonium chloride solution. The aqueous phase was extracted 3 times with 400 ml of ethyl acetate each time, and the combined organic phases were dried with MgSO4. The solvents were removed in vacuo, and the residue was chromatographed on silica gel.

Yield: 2.76 g of tert-butyl (3S,5S,6R)-3-allyl-2-oxo-5,6-diphenyl-3-[1-(2-trimethylsilanylethoxycarbonyl)-(piperidin-4-ylmethyl)]morpholine-4-carboxylate

MS: 551 (M+H-C2H4)

11d) 2-Trimethylsilanylethyl (S)-4-(2-tert-butoxycarbonylamino-2-carboxypent-4-en-yl)-piperidine-1-carboxylate 110 ml of ammonia were condensed at −78° C. 1 g of sodium was added in 3 portions at intervals each of 10 min, and the mixture was stirred for 20 min. Then, at −60° C., a solution of 2.76 g of tert-butyl (3S,5S,6R)-3-allyl-2-oxo-5,6-diphenyl-3-[1-(2-trimethylsilanylethoxycarbonyl)piperidin-4-ylmethyl]morpholine-4-carboxylate and 2.6 ml of ethanol in 50 ml of THF was added dropwise. The mixture was stirred at −45° C. for 1.5 h and the reaction was stopped by adding solid ammonium chloride until the blue color disappeared. The ammonia was then allowed to evaporate off, and 300 ml of water were added to the residue. The THF was removed in vacuo. The aqueous was adjusted to pH 2 with 1 N HCl and extracted 3 times with 200 ml of ethyl acetate each time. The combined organic phases were dried with MgSO4. The solvents were removed in vacuo, and the residue was chromatographed on silica gel.

Yield: 1.3 g of 2-trimethylsilanylethyl (S)-4-(-2-tert-butoxycarbonylamino-2-carboxypent-4-enyl)piperidine-1-carboxylate MS: 373 (M+H-C2H4-tBu)

11e) 2-Trimethylsilanylethyl (S)-4-(2-tert-butoxycarbonylamino-2-methoxycarbonylpent-4-enyl)piperidine-1-carboxylate 1.1 g of 2-trimethylsilanylethyl (S)-(2-tert-butoxycarbonylamino-2-methoxycarbonylpent-4-enyl)piperidine-1-carboxylate were dissolved in 33 ml of methanol and cooled to 0° C. 2.3 ml of a 2 N solution of trimethylsilyldiazomethane in hexane were added dropwise. The mixture was allowed to reach room temperature in the course of 3 h, and then a further 2.3 ml of the trimethylsilyldiazomethane solution were added dropwise. The mixture was stirred for 1 h and then the reaction was stopped by adding 1 ml of acetic acid. After stirring for 30 min, the solvents are removed in vacuo and the residue was chromatographed on silica gel.

Yield: 755 mg of 2-trimethylsilanylethyl (S)-(2-tert-butoxycarbonylamino-2-methoxycarbonylpent-4-enyl)piperidine-1-carboxylate MS: 387 (M+H-C2H4-tBu)

11f) 2-Trimethylsilanylethyl (R)-4-(2-tert-butoxycarbonylamino-2-methoxycarbonyl-4-oxobutyl)piperidine-1-carboxylate 750 mg of 2-trimethylsilanylethyl (S)-4-(2-tert-butoxycarbonylamino-2-methoxycarbonylpent-4-enyl)piperidine-1-carboxylate were dissolved in 30 ml of THF. 852 mg of sodium periodate and 10 ml of water were added. The mixture was then stirred at room temperature for 3 h and filtered through kieselguhr. The filter cake was washed twice with 10 ml of THF each time. The THF was removed in vacuo, and the residue was partitioned between 30 ml of water and 30 ml of ethyl acetate. The pH of the aqueous phase was adjusted to 2 with 1 N HCl solution. The phase were separated and the aqueous phase was extracted twice with 20 ml of ethyl acetate each time. The combined organic phases were dried with MgSO4. The solvents were removed in vacuo and the residue was chromatographed on silica gel.

Yield: 530 mg of 2-trimethylsilanylethyl (R)-4-(2-tert-butoxycarbonylamino-2-methoxycarbonyl-4-oxobutyl)piperidine-1-carboxylate MS: 389 (M+H-C2H4-tBu)

11 g) (3R,6R,7aS)-6-tert-Butoxycarbonylamino-5-oxo-6-[1-(2-trimethylsilanylethoxycarbonyl)piperidin-4-ylmethyl]hexahydropyrrolo[2,1-b]thiazole-3-carboxylic acid 520 mg of 2-trimethylsilanylethyl (R)-4-(2-tert-butoxycarbonylamino-2-methoxycarbonyl-4-oxobutyl)piperidine-1-carboxylate were dissolved in 25 ml of pyridine. 134 mg of L-cysteine were added, and the mixture was heated at 100° C. for 36 h. The pyridine was then removed in vacuo, and the residue was partitioned between 50 ml of ethyl acetate and 50 ml of 0.5 N HCl. The aqueous phase was extracted twice with 20 ml of ethyl acetate each time, and the combined organic phases were dried with MgSO4. The solvents were removed in vacuo, and the residue was chromatographed on silica gel.

Yield: 500 mg of (3R,6R,7aS)-6-tert-butoxycarbonylamino-5-oxo-6-[1-(2-trimethylsilanylethoxycarbonyl)piperidin-4-ylmethyl]hexahydropyrrolo[2,1-b]thiazole-3-carboxylic acid MS. 460 (M+H-C2H4-tBu)

11h) Methyl (3R,6R,7aS)-6-tert-butoxycarbonylamino-5-oxo-6-[1-(2-trimethylsilanylethoxycarbonyl)piperidin-4-ylmethyl]hexahydropyrrolo[2,1-b]thiazole-3-carboxylate 497 mg of (3R,6R,7aS)-6-tert-butoxycarbonylamino-5-oxo-6-[1-(2-trimethylsilanylethoxycarbonyl)piperidin-4-ylmethyl]hexahydropyrrolo[2,1-b]thiazole-3-carboxylic acid were dissolved in 8 ml of methanol and 8 ml of diethyl ether and cooled to 0° C. 914 µl of a 1 N solution of trimethylsilyldiazomethane in hexane were added dropwise. The mixture was stirred for 1 h and then 1 ml of acetic acid was added dropwise. After 1 h, the solvents were removed in vacuo, and the residue was purified by chromatography on silica gel.

Yield: 345 mg of methyl (3R,6R,7aS)-6-tert-butoxycarbonylamino-5-oxo-6-[1-(2-trimethylsilanylethoxycarbonyl)piperidin-4-ylmethyl]hexahydropyrrolo[2,1-b]thiazole-3-carboxylate MS: 474 (M+H-C2H4-tBu)

11i) 2-Trimethylsilanylethyl 4-((3R,6R,7aS)-6-tert-butoxycarbonylamino-3-carbamoyl-5-oxohexahydropyrrolo[2,1-b]thiazol-6-ylmethyl)piperidine-1-carboxylate 340 mg of methyl (3R,6R,7aS)-6-tert-butoxycarbonylamino-5-oxo-6-[1-(2-trimethylsilanylethoxycarbonyl)piperidin-4-ylmethyl]hexahydropyrrolo[2,1-b]thiazole-3-carboxylate were dissolved at 0° C. in 35 ml of an ammonia-saturated methanol solution. The mixture was allowed to reach room temperature in the course of 4 h, and then the solvents were removed in vacuo. The residue was employed without further purification in the next reaction.

Yield: 300 mg of 2-trimethylsilanylethyl 4-((3R,6R,7aS)-6-tert-butoxycarbonylamino-3-carbamoyl-5-oxohexahydropyrrolo[2,1-b]thiazol-6-ylmethyl)piperidine-1-carboxylate MS: 300 (M+H-C2H4-tBu)

11j) 2-Trimethylsilanylethyl 4-((3R,6R,7aS)-6-tert-butoxycarbonylamino-3-cyano-5-oxohexahydropyrrolo[2,1-b]thiazol-6-ylmethyl)piperidine-1-carboxylate 295 mg of 2-trimethylsilanylethyl 4-((3R,6R,7aS)-6-tert-butoxycarbonylamino-3-carbamoyl-5-oxohexahydropyrrolo[2,1-b]thiazol-6-ylmethyl)piperidine-1-carboxylate were dissolved in 20 ml of THF. 166 µl of triethylamine and 91 µl of trifluoroacetic anhydride were successively added dropwise. The mixture was stirred for 1 h and then the same amounts of triethylamine and trifluoroacetic anhydride were again added. After stirring for a further hour, the mixture was partitioned between 150 ml of ethyl acetate and 150 ml of water. The organic phase was dried with MgSO4. The solvent was removed in vacuo and the residue was chromatographed on silica gel.

Yield: 254 mg of 2-trimethylsilanylethyl 4-((3R,6R,7aS)-6-tert-butoxycarbonylamino-3-cyano-5-oxohexahydropyrrolo[2,1-b]thiazol-6-ylmethyl)piperidine-1-carboxylate MS: 441 (M+H-C2H4-tBu)

11 h) (3R,6R,7aS)-6-Amino-5-oxo-6-piperidin-4-ylmethylhexahydropyrrolo[2,1-b]thiazole-3-carbonitrile bistrifluoroacetate 14 mg of 2-trimethylsilanylethyl 4-((3R,6R,7aS)-6-tert-butoxycarbonylamino-3-cyano-5-oxohexahydropyrrolo[2,1-b]thiazol-6-ylmethyl)piperidine-1-carboxylate were stirred in a mixture of 1 ml of trifluoroacetic acid and 200 µl of thioanisole at 0° C. for 40 min. The trifluoroacetic acid was removed in vacuo, and the residue was stirred with diethyl ether.

Yield: 10 mg of (3R,6R,7aS)-6-amino-5-oxo-6-piperidin-4-ylmethylhexahydropyrrolo[2,1-b]thiazole-3-carbonitrile bistrifluoroacetate

MS: 281 (M+H)

The invention claimed is:

1. A compound of the formula I,

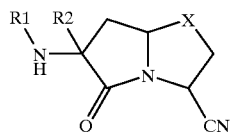

formula I wherein

R1 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl or heterocyclyl, wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, OH, —$CF_3$, $(C_1-C_6)$-alkyl, $(C_2-C_6)$-alkenyl, $(C_2-C_6)$-alkynyl, OR3, NR3R4, COR3, $CO_2$R3, CONR3R4, $(C_1-C_6)$-alkylene-OR3, $(C_1-C_6)$-alkylene-NR3R4, $(C_1-C_6)$-alkylene-SR3, alkylene-SOR3, alkylene-$SO_2$R3, $(C_1-C_6)$-alkylene-COR3, $(C_1-C_6)$-alkylene-COOR3, $(C_1-C_6)$-alkylene-CONR3R4, $(C_1-C_6)$-alkylene-O—P(O)(OR3)$_2$, SR3, SOR3, $SO_2$NR3R4, $SO_2$R3, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl, wherein said $(C_6-C_{10})$-aryl is optionally substituted one or more times by F, Cl, Br, I, CN, $NO_2$, OH, —$CF_3$, $(C_1-C_6)$-alkyl, $(C_2-C_6)$-alkenyl, $(C_2-C_6)$-alkynyl, OR3, NR3R4, COR3, $CO_2$R3 or CONR3R4, and wherein said heterocyclyl is optionally substituted one or more times by F, Cl, Br, I, CN, $NO_2$, OH, —$CF_3$, $(C_1-C_6)$-alkyl, OR3, NR3R4, COR3, $CO_2$R3 or CONR3R4;

R2 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, COOR3, CONR3R4 or CN, wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, —$CF_3$, $(C_2-C_6)$-alkenyl, $(C_2-C_6)$-alkynyl, OR3, OP(O)(OR3)$_2$, NR3R4, NR3CONR3R4, COR3, OCOR3, OCOOR3, COOR3, CONR3R4, OCONR3R4, $(C_1-C_6)$-alkylene-OR3, $(C_1-C_6)$-alkylene-NR3R4, $(C_1-C_6)$-alkylene-NR3SO$_2$R4, $(C_1-C_6)$-alkylene-SR3, alkylene-S(O)R3, alkylene-S(O)$_2$R3, alkylene-S(O)$_2$NR3R4, $(C_1-C_6)$-alkylene-COR3, $(C_1-C_6)$-alkylene-COOR3, $(C_1-C_6)$-alkylene-CONR3R4, SR3, SOR3, $SO_2$R3, $SO_2$NR3R4, NR3$SO_2$R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl;

R3, R4 are each, independently of one another, H, $(C_1-C_6)$-alkyl, —$CF_3$, $(C_3-C_{10})$-cycloalkyl, $(C_6-C_{10})$-aryl, heterocyclyl, $(C_1-C_6)$-alkylene-CONR5R6, CONR5R6, $(C_1-C_6)$-alkylene-COOR5, COOR5, COR5, $(C_1-C_6)$-alkylene-COR5, $(C_1-C_6)$-alkylene-OR5, $(C_1-C_6)$-alkylene-NR5R6, $(C_1-C_6)$-alkylene-SR5, $(C_1-C_6)$-alkylene-S(O)R5, $(C_1-C_6)$-alkylenee-S(O)$_2$R5, S(O)R5, S(O)$_2$R5, $(C_1-C_4)$-alkylene-$(C_6-C_{10})$-aryl or $(C_1-C_4)$-alkylene-heterocyclyl;

R5, R6 are each, independently of one another, H, $(C_1-C_6)$-alkyl, $(C_1-C_6)$-alkylene-$(C_6-C_{10})$-aryl, —$(C_6-C_{10})$-aryl, heterocyclyl or $(C_1-C_6)$-alkylene-heterocyclyl;

X is S, SO or $SO_2$;

and pharmaceutically acceptable salts thereof.

2. The compound of claim 1 wherein:

R1 is H, $(C_1-C_{10})$-alkyl, $(C_3-C_{10})$-cycloalkyl, $(C_2-C_6)$-alkenyl, $(C_2-C_6)$-alkynyl or $(C_6-C_{10})$-aryl, wherein said $(C_1-C_{10})$-alkyl, $(C_3-C_{10})$-cycloalkyl, $(C_2-C_6)$-alkenyl, $(C_2-C_6)$-alkynyl and $(C_6-C_{10})$-aryl radicals are optionally substituted one or more times by F, Cl, Br, I, CN, $NO_2$, OH, —$CF_3$, $(C_1-C_6)$-alkyl, $(C_2-C_6)$-alkenyl, $(C_2-C_6)$-alkynyl, OR3, NR3R4, COR3, $CO_2$R3, CONR3R4, $(C_1-C_6)$-alkylene-OR3, $(C_1-C_6)$-alkylene-NR3R4, $(C_1-C_6)$-alkylene-SR3, alkylene-SOR3, alkylene-$SO_2$R3, $(C_1-C_6)$-alkylene-COR3, $(C_1-C_6)$-alkylene-CO$_2$R3, $(C_1-C_6)$-alkylene-CONR3R4, (C1–C6)-alkylene-O—P(O)(OR3)$_2$, SR3, SOR3, $SO_2$NR3R4, $SO_2$R3, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl or $(C_6-C_{10})$-aryl, wherein said $(C_6-C_{10})$-aryl is optionally substituted one or more times by F, Cl, Br, I, CN, $NO_2$, OH, —$CF_3$, $(C_1-C_6)$-alkyl, $(C_2-C_6)$-alkenyl, $(C_2-C_6)$-alkynyl, OR3, NR3R4, COR3, $CO_2$R3 or CONR3R4;

R2 is H, $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl, heterocyclyl, COR3, CO2R3, CONR3R4 or CN, wherein said $(C_1-C_{10})$-alkyl, $(C_3-C_{10})$-cycloalkyl, $(C_2-C_6)$-alkenyl, $(C_2-C_6)$-alkynyl, $(C_6-C_{10})$-aryl and heterocyclyl radicals are optionally substituted one or more times by F, Cl, Br, I, CN, $NO_2$, SH, $SF_5$, OH, $(C_1-C_6)$-alkyl, —$CF_3$, $(C_2-C_6)$-alkenyl, $(C_2-C_6)$-alkynyl, OR3, OP(O)(OR3)$_2$, NR3R4, NR3CONR3R4, COR3, $CO_2$R3, CONR3R4, OCONR3R4, $(C_1-C_6)$-alkylene-OR3, $(C_1-C_6)$-alkylene-NR3R4, $(C_1-C_6)$-alkylene-NR3$SO_2$R4, $(C_1-C_6)$-alkylene-SR3, alkylene-SOR3, alkylene-$SO_2$R3, alkylene-$SO_2$NR3R4, $(C_1-C_6)$-alkylene-COR3, $(C_1-C_6)$-alkylene-CO$_2$R3, $(C_1-C_6)$-alkylene-CONR3R4, SR3, SOR3, $SO_2$R3, $SO_2$NR3R4, NR3$SO_2$R4, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocyclyl, $(C_3-C_{10})$-cycloalkyl, $(C_6-C_{10})$-aryl or heterocyclyl, wherein said $(C_6-C_{10})$-aryl is optionally substituted one or more times by F, Cl, Br, I, CN, $NO_2$, OH, —$CF_3$, $(C_1-C_6)$-alkyl, $(C_2-C_6)$-alkenyl, $(C_2-C_6)$-alkynyl, OR3, NR3R4, COR3, $CO_2$R3 or CONR3R4, and wherein said heterocyclyl is optionally substituted one or more times by F, Cl, Br, I, CN, NO$_2$, OH, —CF$_3$, (C$_1$–C$_6$)-alkyl, OR3, NR3R4, COR3, CO$_2$R3 or CONR3R4;

R3, R4 are each, independently of one another, H, (C$_1$–C$_6$)-alkyl, —CF$_3$, (C$_3$–C$_{10}$)-cycloalkyl, (C$_6$–C$_{10}$)-aryl, heterocyclyl, (C$_1$–C$_6$)-alkylene-CONR5R6, (C$_1$–C$_6$)-alkylene-CO$_2$R5, (C$_1$–C$_6$)-alkylene-COR5, (C$_1$–C$_6$)-alkylene-OR5, (C$_1$–C$_6$)-alkylene-NR5R6, (C$_1$–C$_6$)-alkylene-SR5, (C$_1$–C$_6$)-alkylene-SOR5, (C$_1$–C$_6$)-alkylene-SO$_2$R5, (C$_1$–C$_4$)-alkylene-(C$_6$–C$_{10}$)-aryl or (C$_1$–C$_4$)-alkylene-heterocyclyl;

R5, R6 are each, independently of one another, H, (C$_1$–C$_6$)-alkyl, (C$_3$–C$_{10}$)-cycloalkyl, (C$_1$–C$_6$)-alkylene-(C$_6$–C$_{10}$)-aryl, —(C$_6$–C$_{10}$)-aryl, heterocyclyl or (C$_1$–C$_6$)-alkylene-(C$_3$–C$_{10}$)-heterocyclyl;

X is S;

and pharmaceutically acceptable salts thereof.

3. The compound of claim 2 wherein:

R1 is H;

R2 is H, (C$_1$–C$_{10}$)-alkyl, (C$_3$–C$_{10}$)-cycloalkyl, (C$_2$–C$_6$)-alkenyl, (C$_2$–C$_6$)-alkynyl, (C$_6$–C$_{10}$)-aryl, heterocyclyl, COR3, CO$_2$R3, CONR3R4 or CN, wherein said (C$_1$–C$_{10}$)-alkyl, (C$_3$–C$_{10}$)-cycloalkyl, (C$_2$–C$_6$)-alkenyl, (C$_2$–C$_6$)-alkynyl, (C$_6$–C$_{10}$)-aryl and heterocyclyl radicals are optionally substituted one or more times by F, Cl, Br, I, CN, NO$_2$, SH, SF$_5$, OH, (C$_1$–C$_6$)-alkyl, —CF$_3$, (C$_2$–C$_6$)-alkenyl, (C$_2$–C$_6$)-alkynyl, OR3, OP(O)(OR3)2, NR3R4, NR3CONR3R4, COR3, OCOR3, CO$_2$R3, CONR3R4, OCONR3R4, (C$_1$–C$_6$)-alkylene-OR3, (C$_1$–C$_6$)-alkylene-NR3R4, (C$_1$–C$_6$)-alkylene-NR3SO$_2$R4, (C$_1$–C$_6$)-alkylene-SR3, alkylene-SOR3, alkylene-SO$_2$R3, alkylene-S(O)$_2$NR3R4, (C$_1$–C$_6$)-alkylene-COR3, (C$_1$–C$_6$)-alkylene-CO$_2$R3, (C$_1$–C$_6$)-alkylene-CONR3R4, SR3, SOR3, SO$_2$R3, SO$_2$NR3R4, NR3SO$_2$R4, (C$_1$–C$_6$)-alkylene-(C$_3$–C$_{10}$)-cycloalkyl, (C$_1$–C$_6$)-alkylene-(C$_6$–C$_{10}$)-aryl, (C$_1$–C$_6$)-alkylene-heterocyclyl, (C$_3$–C$_{10}$)-cycloalkyl, (C$_6$–C$_{10}$)-aryl or heterocyclyl, wherein said (C$_6$–C$_{10}$)-aryl is optionally substituted one or more times by F, Cl, Br, I, CN, NO$_2$, OH, —CF$_3$, (C$_1$–C$_6$)-alkyl, (C$_2$–C$_6$)-alkenyl, (C$_2$–C$_6$)-alkynyl, OR3, NR3R4, COR3, CO$_2$R3 or CONR3R4, and wherein said heterocyclyl is optionally substituted one or more times by F, Cl, Br, I, CN, NO$_2$, OH, —CF$_3$, (C$_1$–C$_6$)-alkyl, OR3, NR3R4, COR3, CO$_2$R3 or CONR3R4;

R3, R4 are each, independently of one another, H, (C$_1$–C$_6$)-alkyl, —CF$_3$, (C$_3$–C$_{10}$)-cycloalkyl, (C$_6$–C$_{10}$)-aryl, heterocyclyl, (C$_1$–C$_6$)-alkylene-CONR5R6, (C$_1$–C$_6$)-alkylene-CO$_2$R5, (C$_1$–C$_6$)-alkylene-COR5, (C$_1$–C$_6$)-alkylene-OR5, (C$_1$–C$_6$)-alkylene-NR5R6, (C$_1$–C$_6$)-alkylene-SR5, (C$_1$–C$_6$)-alkylene-SOR5, (C$_1$–C$_6$)-alkylene-SO$_2$R5, (C$_1$–C$_4$)-alkylene-(C$_6$–C$_{10}$)-aryl or (C$_1$–C$_4$)-alkylene-heterocyclyl;

R5, R6 are each, independently of one another, H, (C$_1$–C$_6$)-alkyl, (C$_3$–C$_{10}$)-cycloalkyl, (C$_1$–C$_6$)-alkylene-(C$_6$–C$_{10}$)-aryl, —(C$_6$–C$_{10}$)-aryl, heterocyclyl or (C$_1$–C$_6$)-alkylene-(C$_3$–C$_{10}$)-heterocyclyl;

X is S;

and pharmaceutically acceptable salts thereof.

4. The compound of claim 3 wherein

R1 is H;

R2 is H, (C$_1$–C$_{10}$)-alkyl, (C$_3$–C$_{10}$)-cycloalkyl, (C$_2$–C$_6$)-alkenyl, (C$_2$–C$_6$)-alkynyl, (C$_6$–C$_{10}$)-aryl, a pyrrolidino, piperidino, hexamethyleneimino, morpholino, piperazino, thiomorpholino or homopiperazino radical, wherein said (C$_1$–C$_{10}$)-alkyl, (C$_3$–C$_{10}$)-cycloalkyl, (C$_2$–C$_6$)-alkenyl, (C$_2$–C$_6$)-alkynyl, (C$_6$–C$_{10}$)-aryl, a pyrrolidino, piperidino, hexamethyleneimino, morpholino, piperazino, thiomorpholino and homopiperazino radicals are optionally substituted one or more times by F, Cl, Br, CN, SF$_5$, OH, (C$_1$–C$_6$)-alkyl, —CF$_3$, (C$_2$–C$_6$)-alkenyl, OR3, NR3R4, NR3CONR3R4, COR3, OCOR3, CO$_2$R3, CONR3R4, OCONR3R4, (C$_1$–C$_6$)-alkylene-OR3, (C$_1$–C$_6$)-alkylene-NR3R4, (C$_1$–C$_6$)-alkylene-NR3SO$_2$R4, (C$_1$–C$_6$)-alkylene-SR3, alkylene-S(O)R3, alkylene-S(O)$_2$R3, alkylene-S(O)$_2$NR3R4, (C$_1$–C$_6$)-alkylene-COR3, (C$_1$–C$_6$)-alkylene-CO$_2$R3, (C$_1$–C$_6$)-alkylene-CONR3R4, SR3, SOR3, SO$_2$R3, SO$_2$NR3R4, NR3SO$_2$R4, (C$_1$–C$_6$)-alkylene-(C$_3$–C$_{10}$)-cycloalkyl, (C$_1$–C$_6$)-alkylene-(C$_6$–C$_{10}$)-aryl, (C$_1$–C$_6$)-alkylene-heterocyclyl, (C$_3$–C$_{10}$)-cycloalkyl, (C$_6$–C$_{10}$)-aryl or heterocyclyl, wherein said (C$_6$–C$_{10}$)-aryl is optionally substituted one or more times by F, Cl, Br, I, CN, OH, —CF$_3$, (C$_1$–C$_6$)-alkyl, OR3, NR3R4, COR3, CO2R3 or CONR3R4, and wherein said heterocyclyl is optionally substituted one or more times by F, Cl, Br, CN, NO$_2$, OH, —CF$_3$, (C$_1$–C$_6$)-alkyl, OR3, NR3R4, COR3, CO2R3 or CONR3R4;

R3, R4 are each, independently of one another, H, (C$_1$–C$_6$)-alkyl, —CF$_3$, (C$_3$–C$_{10}$)-cycloalkyl, (C$_6$–C$_{10}$)-aryl, heterocyclyl, (C$_1$–C$_6$)-alkylene-CONR5R6, (C$_1$–C$_6$)-alkylene-COOR5, (C$_1$–C$_6$)-alkylene-COR5, (C$_1$–C$_6$)-alkylene-OR5, (C$_1$–C$_6$)-alkylene-NR5R6, (C1–C$_6$)-alkylene-SR5, (C$_1$–C$_6$)-alkylene-S(O)R5, (C$_1$–C$_6$)-alkylene-S(O)$_2$R5, (C$_1$–C$_4$)-alkylene-(C$_6$–C$_{10}$)-aryl or (C$_1$–C$_4$)-alkylene-heterocyclyl;

R5, R6 are each, independently of one another, H, (C$_1$–C$_6$)-alkyl, (C$_3$–C$_{10}$)-cycloalkyl, (C$_1$–C$_6$)-alkylene-(C$_6$–C$_{10}$)-aryl, —(C$_6$–C$_{10}$)-aryl, heterocyclyl or (C1–C6)-alkylene-(C$_3$–C$_{10}$)-heterocyclyl;

X is S;

and pharmaceutically acceptable salts thereof.

5. The compound of claim 4 wherein

R1 is H;

R2 is (C$_1$–C$_{10}$)-alkyl, (C$_3$–C$_{10}$)-cycloalkyl, phenyl, (C$_1$–C$_6$)-alkylene-phenyl, a pyrrolidino, piperidino, hexamethyleneimino, morpholino, piperazino, thiomorpholino or homopiperazino radical;

X is S;

and pharmaceutically acceptable salts thereof.

6. A pharmaceutical composition comprising one or more compounds of claim 1 and a pharmaceutically acceptable carrier.

7. The pharmaceutical composition of claim 6 further comprising at least one other active ingredient.

8. A method of reducing blood sugar comprising administering to a patient in need thereof a therapeutically effective amount of a compound of claim 1.

9. A method of treating type 2 diabetes comprising administering to a patient in need thereof a therapeutically effective amount of a compound of claim 1.

10. A method of treating insulin resistance comprising administering to a patient in need thereof a therapeutically effective amount of a compound of claim 1.

* * * * *